US00RE49697E

(19) United States
(12) Reissued Patent
Schwab et al.

(10) Patent Number: US RE49,697 E
(45) **Date of Reissued Patent: *Oct. 17, 2023**

(54) CRYSTALLINE N-[5-(AMINOSULFONYL)-4-METHYL-1,3-THIAZOL-2-YL]-N-METHYL-2-[4-(2-PYRIDINYL)PHENYL] ACETAMIDE MONO MESYLATE MONOHYDRATE HAVING A SPECIFIC PARTICLE SIZE DISTRIBUTION RANGE AND A SPECIFIC SURFACE AREA RANGE FOR USE IN PHARMACEUTICAL FORMULATIONS

(71) Applicant: AiCuris Anti-Infective Cures GmbH, Wuppertal (DE)

(72) Inventors: Wilfried Schwab, Werder (DE); Alexander Birkmann, Wuppertal (DE); Kerstin Paulus, Ratingen (DE); Kurt Vogtli, Oberhofen (CH); Dieter Haag, Ramlinsburg (CH); Stephan Maas, Krefeld (DE); Kristian Ruepp, Berlin (DE)

(73) Assignee: AICURIS ANTI-INFECTIVE CURES AG, Wuppertal (DE)

( * ) Notice: This patent is subject to a terminal disclaimer.

(21) Appl. No.: 17/104,028

(22) Filed: Nov. 25, 2020

Related U.S. Patent Documents

Reissue of:
(64) Patent No.: 10,137,117
Issued: Nov. 27, 2018
Appl. No.: 15/683,127
Filed: Aug. 22, 2017

U.S. Applications:
(60) Division of application No. 14/840,690, filed on Aug. 31, 2015, now Pat. No. 9,889,124, which is a division
(Continued)

(30) Foreign Application Priority Data

Sep. 26, 2011 (EP) ..... 11007803

(51) Int. Cl.
*A61K 31/4439* (2006.01)
*A61K 9/14* (2006.01)
(Continued)

(52) U.S. Cl.
CPC ..... *A61K 31/4439* (2013.01); *A61K 9/145* (2013.01); *A61K 9/16* (2013.01);
(Continued)

(58) Field of Classification Search
CPC ..... A61K 31/4439; A61K 9/145; A61K 9/16; A61K 31/10; A61K 45/06; A61K 31/4402;
(Continued)

(56) References Cited

U.S. PATENT DOCUMENTS 4,892,741 A 1/1990 Ohm et al.
6,348,503 B1 2/2002 Squires
(Continued)

FOREIGN PATENT DOCUMENTS

DE 10129716 A1 1/2003
DE 10129717 A1 1/2003
(Continued)

OTHER PUBLICATIONS

Adalja et al, "Broad-Spectrum Antiviral Agents: A Crucial Pandemic Tool," Expert Review of Anti-infective Therapy, 2019, vol. 17, No. 7, pp. 467-470. (Year: 2019).*
(Continued)

*Primary Examiner* — Alan D Diamond
(74) *Attorney, Agent, or Firm* — MILLEN WHITE ZELANO & BRANIGAN, PC; Brion Heaney

(57) ABSTRACT

The present invention relates to the crystalline mono mesylate monohydrate salt of N-[5-(aminosulfonyl)-4-methyl-1,3-thiazol-2-yl]-N-methyl-2-[4-(2-pyridinyl)phenyl]acetamide in a definite particle size range, particle size
(Continued)

distribution and a specific surface area range, which has demonstrated increased long term stability and release kinetics from pharmaceutical compositions, as well as to pharmaceutical compositions containing said crystalline N-[5-(aminosulfonyl)-4-methyl-1,3-thiazol-2-yl]-N-methyl-2-[4-(2-pyridinyl)phenyl]acetamide mono mesylate monohydrate having the afore-mentioned particle size range, particle size distribution and specific surface area range. Moreover, the present invention relates to the pharmacokinetic and pharmacodynamic in vivo profiles of the resultant free base of N-[5-(aminosulfonyl)-4-methyl-1,3-thiazol-2-yl]-N-methyl-2-[4-(2-pyridinyl)phenyl]-acetamide after administration of the afore-mentioned crystalline N-[5-(aminosulfonyl)-4-methyl-1,3-thiazol-2-yl]-N-methyl-2-[4-(2-pyridinyl)phenyl]-acetamide mono mesylate monohydrate salt to a subject in need thereof.

32 Claims, 13 Drawing Sheets

Related U.S. Application Data of application No. 14/069,850, filed on Nov. 1, 2013, now Pat. No. 9,119,786, which is a continuation-in-part of application No. PCT/EP2012/068958, filed on Sep. 26, 2012.

(51) Int. Cl.

| | |
|---|---|
| ***A61K 9/16*** | (2006.01) |
| ***A61K 31/10*** | (2006.01) |
| ***A61K 45/06*** | (2006.01) |
| ***C07D 417/12*** | (2006.01) |

(52) U.S. Cl.
CPC ..... *A61K 31/10* (2013.01); *A61K 45/06* (2013.01); *C07D 417/12* (2013.01); *Y10T 428/2982* (2015.01)

(58) Field of Classification Search
CPC . C07D 417/12; Y10T 428/2982; A61P 31/00; A61P 31/22
See application file for complete search history.

(56) References Cited

U.S. PATENT DOCUMENTS

| | | | | |
|---|---|---|---|---|
| 7,105,553 | B2 | 9/2006 | Fischer et al. | |
| 7,883,713 | B2 | 2/2011 | Betz et al. | |
| 8,314,112 | B2 | 11/2012 | Leblanc et al. | |
| 8,784,887 | B2 | 7/2014 | Laich et al. | |
| 8,946,217 | B2 | 2/2015 | Shuttleworth et al. | |
| 9,119,786 | B2 | 9/2015 | Schwab et al. | A61P 31/22 |
| 9,238,646 | B2 | 1/2016 | Cheng et al. | |
| 9,340,535 | B2 | 5/2016 | Schwab et al. | A61P 31/20 |
| 9,546,135 | B2 | 1/2017 | Hunt, III et al. | |
| 9,592,225 | B2 | 3/2017 | Schwab et al. | |
| 9,662,360 | B2 | 5/2017 | Squires | |
| 9,889,124 | B2 * | 2/2018 | Schwab | A61K 31/4439 |
| 10,113,515 | B1 | 10/2018 | Yoon et al. | |
| 10,137,117 | B2 | 11/2018 | Schwab et al. | |
| 10,251,893 | B2 | 4/2019 | Cheng et al. | |
| 2004/0006076 | A1 | 1/2004 | Fischer et al. | |
| 2004/0235917 | A1 | 11/2004 | Betz et al. | |
| 2008/0220059 | A1 | 9/2008 | Laich et al. | |
| 2009/0181941 | A1 | 7/2009 | Leblanc et al. | |
| 2012/0258966 | A1 | 10/2012 | Shuttleworth et al. | |
| 2013/0317017 | A1 | 11/2013 | Shuttleworth et al. | |
| 2014/0221433 | A1 | 8/2014 | Schwab et al. | |
| 2014/0294946 | A1 | 10/2014 | Shuttleworth et al. | |
| 2015/0366849 | A1 | 12/2015 | Schwab et al. | |
| 2015/0374676 | A1 | 12/2015 | Itzhaki | |
| 2016/0008341 | A1 | 1/2016 | Schwab et al. | |
| 2020/0121664 | A1 | 4/2020 | Bachhav et al. | |
| 2020/0123145 | A1 | 4/2020 | Bachhav et al. | |
| 2020/0289485 | A1 | 9/2020 | Bachhav et al. | |

FOREIGN PATENT DOCUMENTS

| | | | |
|---|---|---|---|
| JP | 9183728 | A | 7/1997 |
| JP | H09183728 | A | 7/1997 |
| JP | 2007314516 | A | 12/2007 |
| JP | 2009539881 | A | 11/2009 |
| WO | 2001047904 | A1 | 7/2001 |
| WO | 0196874 | A1 | 12/2001 |
| WO | 2001096874 | | 12/2001 |
| WO | 03007946 | A1 | 1/2003 |
| WO | 2003007946 | | 1/2003 |
| WO | 2006/103011 | A2 | 10/2006 |
| WO | 2006103011 | A1 | 10/2006 |
| WO | 14124978 | A2 | 8/2014 |
| WO | 2014124978 | | 8/2014 |

OTHER PUBLICATIONS

English Translation of Office Action corresponding to Japanese Patent Application No. 2014-532367—dated Apr. 26, 2016.
Office Action corresponding to Japanese Patent Application No. 2014-532367—dated Apr. 26, 2016.
Field; Drug Resistance Updates, 2011, 14, 45-51.
International Search Report from PCT/EP2012/068958 dated Oct. 26, 2012.
Ulrich A. K. Betz et al., "Potent in Vivo Antiviral Activity of the Herpes Simplex Virus Primase-Helicase Inhibitor BAY 57-1293" Antimicrobial Agents and Chemotherapy, [Jun. 2002], pp. 1766-1772.
English Translation of Office Action corresponding to Japanese Patent Application No. 2014-5323674—dated Apr. 26, 2016.
Office Action corresponding to Japanese Patent Application No. 2014-5323677—dated Apr. 26, 2016.
Kleymann; Antiviral Chemistry & Chemotherapy 2004, 15, 135-140.
Corey; N Engl J Med 2004, 350, 11-20.

* cited by examiner

CRYSTALLINE N-[5-(AMINOSULFONYL)-4-METHYL-1,3-THIAZOL-2-YL]-N-METHYL-2-[4-(2-PYRIDINYL)PHENYL] ACETAMIDE MONO MESYLATE MONOHYDRATE HAVING A SPECIFIC PARTICLE SIZE DISTRIBUTION RANGE AND A SPECIFIC SURFACE AREA RANGE FOR USE IN PHARMACEUTICAL FORMULATIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present invention relates to the crystalline mono mesylate monohydrate salt of N-[5-(aminosulfonyl)-4-methyl-1,3-thiazol-2-yl]-N-methyl-2-[4-(2-pyridinyl)phenyl]-acetamide in a definite particle size range, particle size distribution and a specific surface area range, which has demonstrated increased long term stability and release kinetics from pharmaceutical compositions, as well as to pharmaceutical compositions containing said crystalline N-[5-(aminosulfonyl)-4-methyl-1,3-thiazol-2-yl]-N-methyl-2-[4-(2-pyridinyl)phenyl]acetamide mono mesylate monohydrate salt having the afore-mentioned particle size range, particle size distribution and specific surface area range.

Furthermore, the present invention relates to the pharmacokinetic (PK) and pharmacodynamic (PD) in vivo profiles of the free base form of N-[5-(aminosulfonyl)-4-methyl-1,3-thiazol-2-yl]-N-methyl-2-[4-(2-pyridinyl)phenyl]-acetamide resulting from crystalline N-[5-(aminosulfonyl)-4-methyl-1,3-thiazol-2-yl]-N-methyl-2-[4-(2-pyridinyl) phenyl]-acetamide mono mesylate monohydrate salt administration to a subject in need thereof, whereby said mono mesylate monohydrate salt is administered in a pharmaceutical composition of the invention. The resulting PK/PD profiles of the free base of N-[5-(aminosulfonyl)-4-methyl-1,3-thiazol-2-yl]-N-methyl-2-[4-(2-pyridinyl)phenyl]-acetamide are useful in methods of treating and/or prophylaxis of herpesviruses and infections caused by herpesviruses and/or preventing from transmission of a herpes virus or herpesviruses in accordance with the invention.

BACKGROUND OF THE INVENTION

Synthesis of N-[5-(aminosulfonyl)-4-methyl-1,3-thiazol-2-yl]-N-methyl-2-[4-(2-pyridinyl)phenyl]acetamide is known from EP 1244641 B1, and the use of acidic components including methanesulfonic acid for the formulation of tablets containing micronized N-[5-(aminosulfonyl)-4-methyl-1,3-thiazol-2-yl]-N-methyl-2-[4-(2-pyridinyl)phenyl]acetamide is disclosed by WO 2006/103011 A1.

It is the objective of the present invention to provide a specific form of a salt of the compound N-[5-(aminosulfonyl)-4-methyl-1,3-thiazol-2-yl]-N-methyl-2-[4-(2-pyridinyl)phenyl]acetamide which exhibits improved properties in regard to stability and bioavailability, and thus makes this specific form of the salt preferable for the manufacturing of pharmaceutical compositions and to provide pharmaceutical compositions containing such a specific salt so that these pharmaceutical compositions exhibit improved properties in regard to stability and bioavailability of the contained specific form of a salt of the compound N-[5-(aminosulfonyl)-4-methyl-1,3-thiazol-2-yl]-N-methyl-2-[4-(2-pyridinyl)phenyl]acetamide. Hereby, it should be noted that in accordance with the invention only the free base form of N-[5-(aminosulfonyl)-4-methyl-1,3-thiazol-2-yl]-N-methyl-2-[4-(2-pyridinyl)phenyl]-acetamide exhibits bioavailability in a subject since the administered crystalline mono mesylate monohydrate salt of N-[5-(aminosulfonyl)-4-methyl-1,3-thiazol-2-yl]-N-methyl-2-[4-(2-pyridinyl)phenyl]-acetamide turns in vivo into the corresponding free base form.

Accordingly, another aspect of the present invention is directed to the PK profiles resulting from administration of the crystalline mono mesylate monohydrate salt of N-[5-(aminosulfonyl)-4-methyl-1,3-thiazol-2-yl]-N-methyl-2-[4-(2-pyridinyl)phenyl]-acetamide in vivo, when administered in a pharmaceutical composition of the instant invention to a subject in need thereof. The PK in vivo profiles of the free base of N-[5-(aminosulfonyl)-4-methyl-1,3-thiazol-2-yl]-N-methyl-2-[4-(2-pyridinyl)phenyl]-acetamide enable sufficient absolute bioavailability of 70%±30% thereof.

The objectives of the present invention are solved by the teaching of the independent claims. Further advantageous features, aspects, and details of the invention are evident from the dependent claims, the description, the drawings (Figs.), and the examples of the present application.

DESCRIPTION OF THE INVENTION

At room temperature, there are four polymorphic forms and an amorphous form of the free base of N-[5-(aminosulfonyl)-4-methyl-1,3-thiazol-2-yl]-N-methyl-2-[4-(2-pyridinyl)-phenyl]acetamide. In addition, several solvates can be detected for the free base of N-[5-(aminosulfonyl)-4-methyl-1,3-thiazol-2-yl]-N-methyl-2-[4-(2-pyridinyl)-phenyl]acetamide depending on the solvent. Based on the existence of the afore-mentioned forms of the free base of N-[5-(aminosulfonyl)-4-methyl-1,3-thiazol-2-yl]-N-methyl-2-[4-(2-pyridinyl)-phenyl]acetamide at room temperature, no conclusion on thermic stability can be drawn. Hence, the free base of N-[5-(aminosulfonyl)-4-methyl-1,3-thiazol-2-yl]-N-methyl-2-[4-(2-pyridinyl)-phenyl]acetamide is not suitable for a long-term stable formulation, because long-term properties of the free base of N-[5-(aminosulfonyl)-4-methyl-1,3-thiazol-2-yl]-N-methyl-2-[4-(2-pyridinyl)-phenyl]acetamide cannot be determined. In addition, the low solubility is responsible for unfavorable drug release and resorption properties compared to the crystalline mono mesylate monohydrate salt of N-[5-(aminosulfonyl)-4-methyl-1,3-thiazol-2-yl]-N-methyl-2-[4-(2-pyridinyl)phenyl]-acetamide.

Surprisingly, it was found that the crystalline mono mesylate monohydrate salt of N-[5-(aminosulfonyl)-4-methyl-1,3-thiazol-2-yl]-N-methyl-2-[4-(2-pyridinyl)phenyl]acetamide overcomes all drawbacks of the free base or other salts, if said crystalline mono mesylate monohydrate salt has a specific PSD (particle size distribution), PSR (particle size range) and SSA (specific surface area). This also results in advantageous PK/PD in vivo profiles of the resultant free base of N-[5-(aminosulfonyl)-4-methyl-1,3-thiazol-2-yl]-N-methyl-2-[4-(2-pyridinyl)phenyl]acetamide as the pharmacologic active component resulting from administration of the crystalline mono mesylate monohydrate salt of N-[5-(aminosulfonyl)-4-methyl-1,3-thiazol-2-yl]-N-methyl-2-[4-(2-pyridinyl)phenyl]acet-amide. Thus, the present invention relates to the crystalline N-[5-(aminosulfonyl)-4-methyl-1,3-thiazol-2-yl]-N-methyl-2-[4-(2-pyridinyl)-phenyl]acetamide mono methanesulfonic acid monohydrate of the following formula

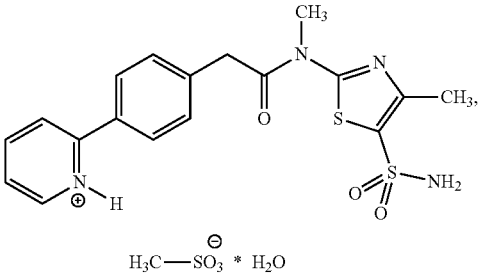

wherein the crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles have a particle size range from 1 to 500 μm, a particle size distribution which is defined by d(0.1) from 2 to 100 μm, d(0.5) from 30 to 210 μm and d(0.9) from 70 to 400 μm and a specific surface area of less than 1.0 $m^2/g$.

The synthesis of N-[5-(aminosulfonyl)-4-methyl-1,3-thiazol-2-yl]-N-methyl-2-[4-(2-pyridinyl)phenyl]acetamide mono methanesulfonic acid monohydrate is shown below

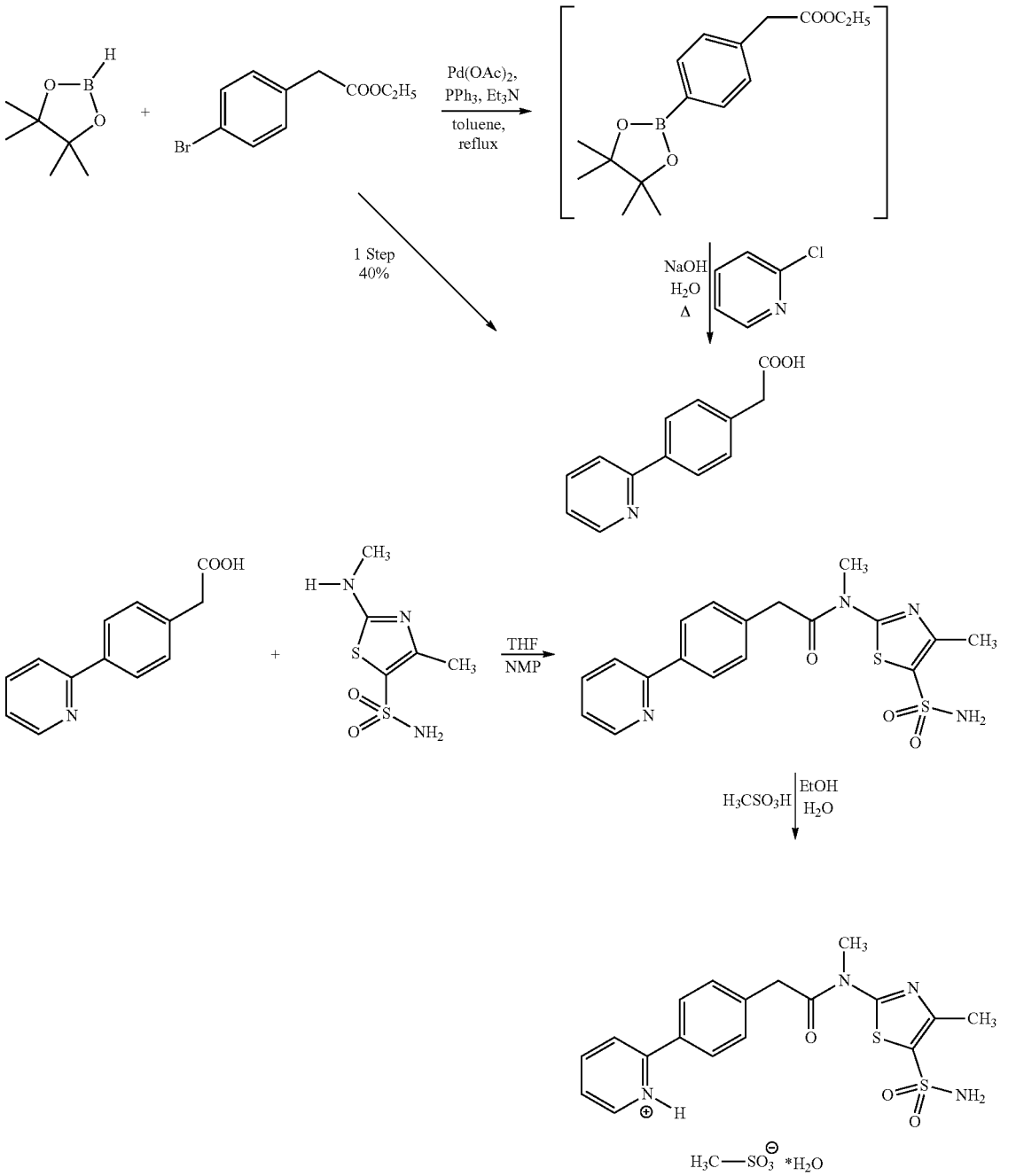

The above synthesis uses a boronic acid derivative, a borolane or a borinane reagent which is reacted with ethyl-4-bromophenylacetate in order to obtain the key intermediate (4-pyridin-2-ylphenyl) acetic acid in a single stage with an overall yield of about 40% of theory. The (4-pyridin-2-ylphenyl)acetic acid is reacted with 4-methyl-2-(methylamino)-1,3-thiazole-5-sulfonamide to the free base of N-[5-(aminosulfonyl)-4-methyl-1,3-thiazol-2-yl]-N-methyl-2-[4-(2-pyridinyl)phenyl]acetamide, which is then converted to the definite crystalline mono mesylate monohydrate salt exhibiting a specific PSD, PSR and SSA. The single reaction steps for the synthesis of the N-[5-(aminosulfonyl)-4-methyl-1,3-thiazol-2-yl]-N-methyl-2-[4-(2-pyridinyl)phenyl]acetamide mono mesylate monohydrate salt are summarized below.

Step A: Reacting compound A of the following general formula A*

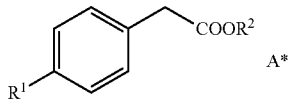

A* wherein $R^1$ represents a leaving group and $R^2$ represents an alkyl residue with 1 to 6 carbon atoms or a cycloalkyl residue with 3 to 6 carbon atoms, with a boronic acid derivative, borolane, borinane or diboronic acid reagent under elimination of $R^1$—H or $R^1$—B $(OR)_2$ and formation of an intermediate boronic acid derivative of compound A, wherein preferred catalysts for the reaction are the reagent systems palladium acetate with triethylamine and with triphenylphosphine or $PdCl_2(PPh_3)_2$ with triethylamine, wherein the intermediate boronic acid derivative is then reacted with the pyridine compound B of the following general formula B*

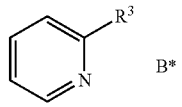

B* wherein $R^3$ represents a leaving group under basic conditions in order to obtain the (4-pyridin-2-ylphenyl)acetic acid as an alkaline solution of the corresponding carboxylate salt.

The resulting (4-pyridin-2-ylphenyl)acetic acid was purified by simple washing steps at different pH and filtration steps followed by precipitation or crystallization, preferably by properly adjusting the pH of an aqueous acidic solution of (4-pyridin-2-ylphenyl)acetic acid with an appropriate amount of base to 3.5-5.0, preferably 3.8-4.7. Beside the simple washing and filtration steps, no further purification of the (4-pyridin-2-ylphenyl)acetic acid or any of the intermediates, as for instance by recrystallization or chromatography, is required.

Step B: Reacting (4-pyridin-2-ylphenyl)acetic acid obtained from step A with 4-methyl-2-(methylamino)-1,3-thiazole-5-sulfonamide

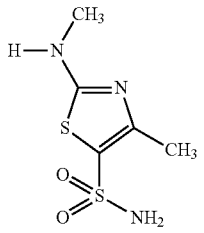

in order to obtain N-[5-(aminosulfonyl)-4-methyl-1,3-thiazol-2-yl]-N-methyl-2-[4-(2-pyridinyl)phenyl]acetamide of the formula

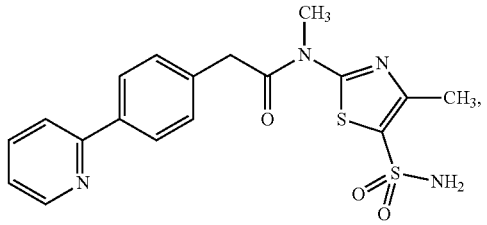

The free base of N-[5-(aminosulfonyl)-4-methyl-1,3-thiazol-2-yl]-N-methyl-2-[4-(2-pyridinyl)-phenyl]acetamide is thereafter most preferably converted (as step C) to the so far unknown monohydrate of the mono mesylate salt of N-[5-(aminosulfonyl)-4-methyl-1,3-thiazol-2-yl]-N-methyl-2-[4-(2-pyridinyl)phenyl]acetamide. The obtained N-[5-(aminosulfonyl)-4-methyl-1,3-thiazol-2-yl]-N-methyl-2-[4-(2-pyridinyl)phenyl]acetamide mono mesylate monohydrate is then formulated as particles having a particle size in the range from 1 μm to 500 μm and a particle size distribution defined by d(0.1) from 2 to 100 μm, d(0.5) from 30 to 210 μm and d(0.9) from 70 to 400 μm and a specific surface area of the particles less than 1.0 $m^2/g$, and more preferably a PSD defined by d(0.1) from 10 to 75 μm, d(0.5) from 100 to 175 μm, d(0.9) from 200 to 350 μm with a SSA of the particles less than 0.3 $m^2/g$.

In the above synthesis, the term "leaving group" as used herein is a molecular fragment that departs with a pair of electrons in heterolytic bond cleavage. Leaving groups can be anions or neutral molecules. Common anionic leaving groups are halides such as $Cl^-$, $Br^-$, and $I^-$, and sulfonate esters, such as para-toluenesulfonate ("tosylate", $TsO^-$), trifluoromethanesulfonate ("triflate", $TfO^-$, $CF_3SO_2O^-$), benzenesulfonate ("besylate," $C_6H_5SO_2O^-$) or methanesulfonate ("mesylate", $MsO^-$).

General formula A* as shown below

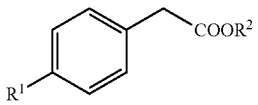

A* covers all phenyl acetic acid esters having a leaving group on the phenyl residue in position 4.

Thus $R^1$ preferably represents —F, —Cl, —Br, —I, —OMs, —OTf and —OTs. The group "—OMs" refers to —OMesylate, the group "—OTf" refers to —OTriflate and the group "—OTs" refers to —OTosylate.

The group $R^2$ represents an alkyl residue with 1 to 6 carbon atoms or a cycloalkyl residue with 3 to 6 carbon atoms, and preferably —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$C_6H_{13}$, cyclo-$C_3H_5$, cyclo-$C_4H_7$, cyclo-$C_5H_9$, cyclo-$C_6H_{11}$. More preferred are —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, and —$C_5H_{11}$. Especially preferred are —$CH_3$, —$C_2H_5$, —$C_3H_7$, and —$CH(CH_3)_2$.

Various boronic acid derivatives, borolanes and borinanes as well as the corresponding diboronic acid derivatives can be used in step A of the inventive synthesis disclosed herein. Preferred are borolanes of the following general formula:

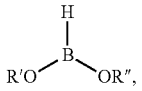

wherein R' and R" are independently of each other any substituted or unsubstituted, linear or branched alkyl group with 1 to 10 carbon atoms or cycloalkyl group with 3 to 10 carbon atoms, or R' and R" can also form together with the boron atom a heterocyclic ring wherein R' and R" together form a substituted or unsubstituted, linear or branched alkene group with 2 to 10 carbon atoms. Preferably R' and R" represent independently of each other —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, and —$C_5H_{11}$. The cyclic borolanes are preferred.

The following borolanes, borinanes and diboronic acid derivatives are preferred:

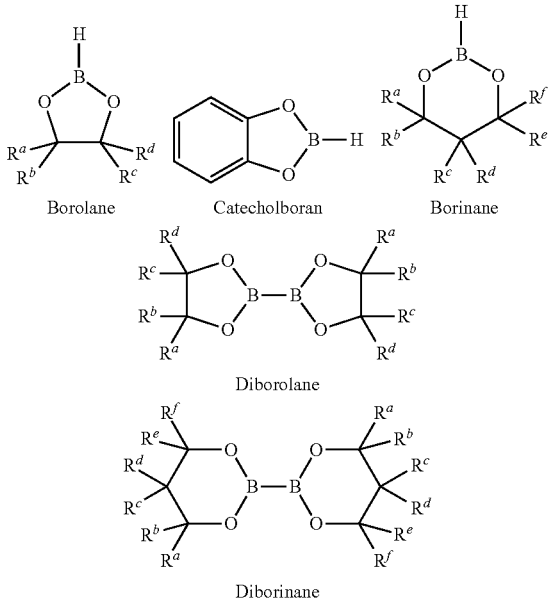

wherein $R^a$, $R^b$, $R^c$, $R^d$, $R^e$ and $R^f$ represent independently of each other a substituted or unsubstituted, linear or branched alkyl group with 1 to 10 carbon atoms or cycloalkyl group with 3 to 10 carbon atoms. Preferred are the linear alkyl residues with 1 to 6 carbon atoms, and most preferred are —$CH_3$, —$C_2H_5$, —$C_3H_7$ and —$CH(CH_3)_2$.

Especially preferred examples for the above borone containing compounds are 4,4,5,5-tetramethyl[1,3,2]dioxaborolane (pinacolborane), [1,3,2]dioxaborolane, [1,3,2]dioxaborinane, 5,5-dimethyl[1,3,2]dioxaborinane, 4,6,6-trimethyl[1,3,2]-dioxaborinane, 4,4,6,6-tetramethyl[1,3,2]-dioxaborinane, 4,4,5,5,6,6-hexamethyl[1,3,2]-dioxaborinane, diisopropoxyborane, hexahydrobenzo[1,3,2]di-oxaborole, 9,9-dimethyl-3,5-dioxa-4-bora-tricyclo[6.1.1.$6^{2,6}$]decane, 6,9,9-trimethyl-3,5-dioxa-4-bora-tricyclo[6.1.1.$6^{2,6}$]decane, B2Pin2(bis(pinacolato)diborane), bis(nepentyl glycolato)diboron and catecholboran.

In step A this boronic acid derivative, borolane, borinane or diboronic acid reagent is reacted with a compound A of general formula A* in order to obtain an intermediate borolan or borinane reagent which is not isolated and purified. This reaction may be supported by the use of either catalysts prepared in situ by combination of palladium salts such as $[Pd(OAc)_2]$ and $PdCl_2$ with triphenylphosphine ($PPh_3$), tri-ortho-tolylphosphine ($P(o\text{-}Tol)_3$), tricyclohexylphosphine ($PCy_3$), tri-tert.-butylphosphine, 1,4-Bis-(diphenylphosphino)-butane (dppb), and 1,1'-Bis-(diphenylphosphino)-ferrocene dppf or preformed catalysts such as $Pd(PPh_3)_2Cl_2$, $Pd(PPh_3)_4$, Fibrecat 1032, and $Pd(dppf)Cl_2$ in the presence of a variety of organic and inorganic bases such as triethylamine ($Et_3N$), NaOAc, KOAc, and $K_3PO_4$. For this reaction heating to temperature between 70° C. and 150° C., preferably between 80° C. and 130° C., more preferably between 90° C. and 110° C. is used. Moreover aprotic and preferably apolar solvents and preferably aromatic solvents such as benzene or toluene or xylenes are used.

The intermediate boronic acid reagent is subsequently reacted with a pyridinyl compound of the general formula B*, wherein $R^3$ represents a leaving group. Thus, $R^3$ represents —F, —Cl, –Br, –I, —OMs, —OTf and —OTs and preferably —Cl or —Br.

The corresponding (4-pyridin-2-ylphenyl)acetic acid ester is in situ treated with a aqueous base in order to cleave the ester linkage. It could be advantageous to heat the reaction mixture during the coupling/saponification step to moderate temperature and preferably to temperature between 40° C. and 90° C., more preferably between 45° C. and 80° C., still more preferably between 50° C. and 70° C. and most preferably between 55° C. and 65° C.

After purification and isolation of the key intermediate (4-pyridin-2-ylphenyl)acetic acid, the (4-pyridin-2-ylphenyl)acetic acid was obtained in a yield of about 40% of theory including only one isolation and purification step.

Thereafter the (4-pyridin-2-ylphenyl)acetic acid was reacted with 4-methyl-2-(methylamino)-1,3-thiazole-5-sulfonamide of the formula

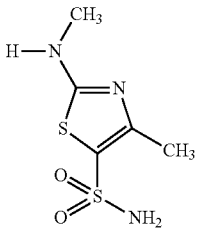

which was prepared according to the synthesis disclosed in EP 1244641 B1 in order to obtain N-[5-(aminosulfonyl)-4-methyl-1,3-thiazol-2-yl]-N-methyl-2-[4-(2-pyridinyl)phenyl]acetamide of the formula

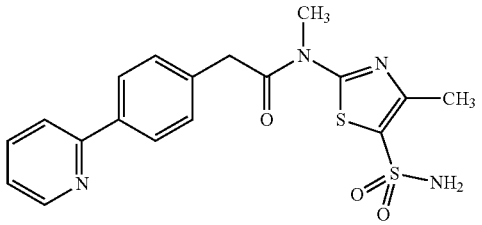

This N-[5-(aminosulfonyl)-4-methyl-1,3-thiazol-2-yl]-N-methyl-2-[4-(2-pyridinyl)-phenyl]acetamide was thereafter converted to the crystalline mono mesylate monohydrate salt, wherein the typical particle size range is from 1 to 500 μm and the particle size distribution is preferably defined by d(0.1) from 2 to 100 μm, d(0.5) from 30 to 210 μm and d(0.9) from 70 to 400 μm and wherein the crystalline particles have a specific surface area of less than 1.0 $m^2/g$, and more preferably the PSD is defined by d(0.1) from 10 to 75 μm, d(0.5) from 100 to 175 μm, d(0.9) from 200 to 350 μm and the SSA of the particles is less than 0.3 $m^2/g$.

The parameter d(0.1) refers to the mesh size of a single notional sieve allowing 10% of the total of all particles of the sample to pass. Thus d(0.1)=2-100 μm means that the upper limit of the particle size range defining the 10% of smallest particles in the sample is between 2 μm to 100 μm. Thus 10% of the total particles have a particle size of not more than d(0.1) meaning in this case that they have a maximum size of 2 μm to 100 μm.

Accordingly, the parameter d(0.5) refers to the mesh size of a single notional sieve allowing 50% of the total of all particles of the sample to pass. Thus d(0.5)=30-210 μm means that the upper limit of the particle size range defining the notional half of the sample containing the smaller particles is between 30 μm to 210 μm. Thus, 50% of the total of all particles have a particle size of not more than d(0.5) meaning in this case that they have a maximum size of 30 μm to 210 μm. Accordingly, the parameter d(0.9) refers to the mesh size of a single notional sieve allowing 90% of the total of all particles of the sample to pass i.e. only 10% of the sample is retained. Thus, d(0.9)=70-400 μm means that the lower limit of the particle size range defining the 10% of largest particles in the sample is between 70 μm to 400 μm. Thus 90% of all particles have a particle size of not more than d(0.9) meaning in this case that they have a maximum size of 70 μm to 400 μm.

It is furthermore preferred that the particle size of the crystalline N-[5-(amino-sulfonyl)-4-methyl-1,3-thiazol-2-yl]-N-methyl-2-[4-(2-pyridinyl)-phenyl]acetamide mesylate monohydrate particles is within the range of 1 μm to 500 μm, preferably in the range of 1.5 μm to 450 μm and more preferably in the range of 2 μm to 400 μm. Thus, the particle size range (PSR) of the mesylate monohydrate is from 1.0 μm to 500 μm, preferably from 1.5 μm to 450 μm, more preferably from 2.0 μm to 400 μm, still more preferably from 2.5 μm to 300 μm and most preferably from 3.0 μm to 250 μm. If the PSR is not mentioned at all or if reference to the PSR is made without stating a definite value, it shall be referred to a particle size range from 1 to 500 μm.

Moreover, it is preferred that the particle size distribution of the crystalline N-[5-(amino-sulfonyl)-4-methyl-1,3-thiazol-2-yl]-N-methyl-2-[4-(2-pyridinyl)-phenyl]acet-amide mono mesylate monohydrate particles is characterized by d(0.1) from 4 to 100 μm, d(0.5) from 30 to 210 μm and d(0.9) from 70 to 400 μm, more preferably d(0.1) from 6 to 95 μm, d(0.5) from 50 to 200 μm and d(0.9) from 100 to 390 μm, still more preferably d(0.1) from 7 to 90 μm, d(0.5) from 70 to 190 μm and d(0.9) from 130 to 380 μm, still more preferably d(0.1) from 8 to 85 μm, d(0.5) from 80 to 185 μm and d(0.9) from 160 to 370 μm, still more preferably d(0.1) from 9 to 80 μm, d(0.5) from 90 to 180 μm and d(0.9) from 180 to 360 μm, still more preferably d(0.1) from 10 to 75 μm, d(0.5) from 100 to 175 μm and d(0.9) from 200 to 350 μm and most preferably d(0.1) from 11 to 70 μm, d(0.5) from 110 to 170 μm and d(0.9) from 220 to 340 μm.

Furthermore, it is preferred that the specific surface area of the crystalline particles is less than 1.0 $m^2/g$, more preferably less than 0.9 $m^2/g$, still more preferably less than 0.8 $m^2/g$, still more preferably less than 0.7 $m^2/g$, still more preferably less than 0.6 $m^2/g$, still more preferably less than 0.5 $m^2/g$, still more preferably less than 0.4 $m^2/g$ and most preferably the SSA of the particles is less than 0.3 $m^2/g$.

In a certain aspect of the present invention said specific surface area is typically greater than about 0.01 to 0.06 $m^2/g$, the lower limit not being particularly important.

Accordingly, in another aspect of the invention the specific surface area is within a range of 0.01 to 0.99 $m^2/g$, preferably within a range of 0.05 to 0.99 $m^2/g$, even more preferably within a range of 0.06 to 0.99 $m^2/g$, most preferred within a range of 0.06 to 0.29 $m^2/g$.

As used herein the terms "mono mesylate monohydrate", or "crystalline mono mesylate monohydrate", or "mono methanesulfonic acid monohydrate", or "crystalline mono methanesulfonic acid monohydrate", or "crystalline N-[5-(amino-sulfonyl)-4-methyl-1,3-thiazol-2-yl]-N-methyl-2-[4-(2-pyridinyl)-phenyl]acetamide mono mesylate monohydrate", or "N-[5-(amino-sulfonyl)-4-methyl-1,3-thiazol-2-yl]-N-methyl-2-[4-(2-pyridinyl)-phenyl]acetamide mono methanesulfonic acid monohydrate" refers to the crystalline N-[5-(amino-sulfonyl)-4-methyl-1,3-thiazol-2-yl]-N-methyl-2-[4-(2-pyridinyl)-phenyl]-acetamide mono methanesulfonic acid monohydrate having the PSD, PSR and SSA as defined herein. Thus, these terms ever denote the specific mono mesylate monohydrate salt in accordance with the invention, whereas the term "free base of N-[5-(amino-sulfonyl)-4-methyl-1,3-thiazol-2-yl]-N-methyl-2-[4-(2-pyridinyl)-phenyl]acetamide", "free base form", and "free base" ever denote the free base form of N-[5-(amino-sulfonyl)-4-methyl-1,3-thiazol-2-yl]-N-methyl-2-[4-(2-pyridinyl)-phenyl]acetamide, which also is ever the pharmacologically active form of N-[5-(amino-sulfonyl)-4-methyl-1,3-thiazol-2-yl]-N-methyl-2-[4-(2-pyridinyl)-phenyl]acetamide in the human body.

With the context of the present invention and the free base of N-[5-(amino-sulfonyl)-4-methyl-1,3-thiazol-2-yl]-N-methyl-2-[4-(2-pyridinyl)-phenyl]acetamide, "pharmacologically active" means acting antiviral in methods of treating and/or prophylaxis of herpesviruses and infections caused by herpesviruses and/or preventing from transmission of a herpes virus or herpesviruses.

The crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to the invention is preferably combined with and used in combination with acetylsalicylic acid, trifluridine, idoxuridine, foscarnet, cidofovir, ganciclovir, aciclovir, penciclovir, valaciclovir, famciclovir and/or valganciclovir. Especially preferred are combinations with acetylsalicylic acid or aciclovir or penciclovir or acetylsalicylic acid and aciclovir or acetylsalicylic acid and penciclovir.

The inventive mono mesylate monohydrate or the aforementioned drug combinations are preferably used for the manufacture of a pharmaceutical composition for the treatment and/or prophylaxis of infectious diseases and the prevention of transmission of an infectious disease and especially infectious diseases caused by herpes simplex viruses.

The crystalline N-[5-(amino-sulfonyl)-4-methyl-1,3-thiazol-2-yl]-N-methyl-2-[4-(2-pyridinyl)-phenyl]acetamide mono mesylate monohydrate obtainable according to the above disclosed synthesis is then used to prepare a pharmaceutical composition thereof, wherein the crystalline N-[5-(amino-sulfonyl)-4-methyl-1,3-thiazol-2-yl]-N-methyl-2-[4-(2-pyridinyl)phenyl]acetamide mono mesylate monohydrate has the particle size distribution (PSD), specific surface area (SSA) and particle size range (PSR) as defined herein. To this pharmaceutical composition acetylsalicylic acid, trifluridine, idoxuridine, foscarnet, cidofovir, ganciclovir, aciclovir, penciclovir, and/or their respective prodrugs valaciclovir, famciclovir and/or valganciclovir might be added. Some suppliers use the name acyclovir instead of aciclovir. Moreover, these pharmaceutical compositions are preferably solid pharmaceutical compositions without solvents, diluents, or liquids exhibiting solubilizing properties for the active pharmaceutical ingredient (hereinafter abbreviated API) so that the particles are not dissolved and remain unaltered in regard to their particle size distribution, particle size range and specific surface area.

As used herein, the acronym "API" ever denotes the crystalline N-[5-(amino-sulfonyl)-4-methyl-1,3-thiazol-2-yl]-N-methyl-2-[4-(2-pyridinyl)-phenyl]acetamide mono mesylate monohydrate salt.

In WO2006/103011A a wet granulation process for tablet preparation is described for the free base form using diverse acids including methanesulfonic acid. In a series of crystallization experiments starting from N-[5-(aminosulfonyl)-4-methyl-1,3-thiazol-2-yl]-N-methyl-2-[4-(2-pyridinyl)-phenyl]acetamide and benzoic acid, lactic acid, and sulphuric acid, a crystalline salt (apparently occurring in different polymorphic forms) could only be isolated with sulphuric acid. Nevertheless, using sulphuric acid in the wet granulation process resulted in a tablet exhibiting unfavorable dissolution properties (see Table 3 of WO2006/103011A). Repeating the wet granulation process (cf. example 5 of WO2006/103011A) using 1 equivalent methanesulfonic acid as acidic component resulted in a granulate, which contained a mixture of the crystalline free base form and mesylate monohydrate salt (ca. 90:10, detectable by comparison of the X-ray powder diffraction spectra, which did not change significantly over 4 weeks at 40° C. (see FIG. 1). This mesylate/free base mixture had been found unsuitable for a tablet formulation, because of low solubility and dissolution behavior, the occurrence of at least four polymorphic forms and the additional risk of further interconversion between base and salt form under long term storage (also depending on the water content and hygroscopicity of the tablet mixture). Thus, it was very surprising that a definite mono mesylate monohydrate salt of N-[5-(aminosulfonyl)-4-methyl-1,3-thiazol-2-yl]-N-methyl-2-[4-(2-pyridinyl)-phenyl]acetamide could be obtained and that this definite mono mesylate monohydrate salt of N-[5-(aminosulfonyl)-4-methyl-1,3-thiazol-2-yl]-N-methyl-2-[4-(2-pyridinyl)-phenyl]acetamide with the characteristic PSR, PSD and SSA as disclosed herein overcame all problems of the state of the art and provided the opportunity to prepare stable, long-term stable, and pharmacologically applicable pharmaceutical compositions, which showed clear advantages for solid formulations.

For the purpose of tabletting, the flowability of a mixture of N-[5-(aminosulfonyl)-4-methyl-1,3-thiazol-2-yl]-N-methyl-2-[4-(2-pyridinyl)-phenyl]acetamide mono methanesulfonic acid monohydrate having the PSR, PSD and SSA as defined herein with usual pharmaceutical ingredients is improved with larger particles and narrower particle size distribution. As particle size decreases, several interparticulate forces such as mechanical interlocking, hydrogen bonding, electrostatic, and van der Waals forces can predominate over gravity. These forces act in the surface of the particles and smaller particles have larger surface area in relation to their mass than larger ones. In addition, these varying results may be due to differences in the flowability measurement set-ups, humidity of the air, and/or particle properties such as original particle size. A broad particle size distribution induces segregation that influences tabletting force, tablet weight and the content uniformity of the tablets. Broad particle size distribution causes more segregation problems during tabletting than a granule batch with smaller size distribution within a defined range. Thus, due to various possible particle size ranges, particle size distributions and specific surface areas adjustable by various techniques, it was unforeseeable for the skilled person that the ranges for PSD, SSA and PSR as defined herein are the most suitable for preparing pharmaceutical compositions. Particularly, it was unforeseeable for the skilled person that the ranges for PSD, SSA and PSR of the crystalline mono mesylate monohydrate salt of N-[5-(aminosulfonyl)-4-methyl-1,3-thiazol-2-yl]-N-methyl-2-[4-(2-pyridinyl)-phenyl]acetamide as defined herein lead to advantageous PK/PD in vivo profiles of its pharmacologically active free base form as exemplarily depicted in the FIGS. 9-13. Said Figures show exemplarily PK/PD in vivo profiles of the resultant free base form in vivo, when administered orally either as single dose or in the form of multiple dosages as crystalline mono mesylate monohydrate salt of N-[5-(aminosulfonyl)-4-methyl-1,3-thiazol-2-yl]-N-methyl-2-[4-(2-pyridinyl)-phenyl]acetamide.

The narrow particle size distribution of the crystalline form of N-[5-(aminosulfonyl)-4-methyl-1,3-thiazol-2-yl]-N-methyl-2-[4-(2-pyridinyl)-phenyl]acetamide mono methanesulfonic acid monohydrate, e.g. for a given mean particle size, they have fewer large and small particles, is advantageous for direct compression as a method of tablet manufacturing. The resulting particle size distribution of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein the PSR, PSD and SSA is as defined herein and preferably wherein the particle size distribution is defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, has physical characteristics, which are particularly adapted to be able to allow manufacturing by direct compression without a wet or dry granulation step.

According to the invention, it is preferred that at least 65 v/v %, more preferably at least 70 v/v %, even more preferably at least 80 v/v %, even more preferably at least 85 v/v %, even more preferably at least 90 v/v %, even more preferably at least 95 v/v % and most preferred at least 99 v/v % of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles fall in a particle size range of from 2 to 400 μm. Moreover it is preferred that 40 v/v % N-[5-(aminosulfonyl)-4-methyl-1,3-thiazol-2-yl]-N-methyl-2-[4-(2-pyridinyl)-phenyl]acetamide mono methanesulfonic acid monohydrate particles fall in a particle size range of from 2-250 μm.

It was surprisingly found that the use of crystalline N-[5-(aminosulfonyl)-4-methyl-1,3-thiazol-2-yl]-N-methyl-2-[4-(2-pyridinyl)-phenyl]acetamide mono methanesulfonic acid monohydrate in particulate form, wherein the PSR, PSD and SSA is as defined herein and preferably wherein the particle size distribution is defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ in the final blend shows improved free-flowing and cohesive powder characteristics and displays cohesive briquetting and dry granulation behavior, which effects are significant for efficient and robust direct compression.

If too many crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles are present whose particle size is lower than about 4 μm, picking and sticking tend to be caused in the later processing. If too many crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles are present whose particle size is larger than about 400 μm, the compressibility becomes too poor. Therefore, it is observed that at least 65 v/v % of crystalline N-[5-(aminosulfonyl)-4-methyl-1,3-thiazol-2-yl]-N-methyl-2-[4-(2-pyridinyl)-phenyl]acetamide mono methanesulfonic acid monohydrate fall in a particle size range of from 2 to 400 μm, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$.

When processing crystalline N-[5-(aminosulfonyl)-4-methyl-1,3-thiazol-2-yl]-N-methyl-2-[4-(2-pyridinyl)-phenyl]acetamide mono methanesulfonic acid monohydrate, its particle size distribution remains substantially unchanged, typically it remains totally unchanged. In view of improved overall characteristics, it is preferred that at least 65 v/v %, more preferably at least 70 v/v %, even more preferably at least 80 v/v %, even more preferably at least 85 v/v %, even more preferably at least 90 v/v %, even more preferably at least 95 v/v % and most preferred at least 99 v/v % of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles have the PSR, PSD and SSA as defined herein and more preferably fall in a particle size range of from 2 to 400 μm, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and still more preferably defined by d(0.1) from 10 to 75 μm, d(0.5) from 100 to 175 μm, d(0.9) from 200 to 350 μm with a specific surface area of the particles less than 0.3 $m^2/g$.

A further advantage of the tablets according to the invention is that the tablet will have an optimized dissolution rate based on its particle size distribution of the crystalline form of N-[5-(aminosulfonyl)-4-methyl-1,3-thiazol-2-yl]-N-methyl-2-[4-(2-pyridinyl)-phenyl]acetamide mono methanesulfonic acid monohydrate which has the PSD, PSR and SSA as defined herein and thus, the drug may be absorbed into the blood stream much faster compared to the free base form of N-[5-(aminosulfonyl)-4-methyl-1,3-thiazol-2-yl]-N-methyl-2-[4-(2-pyridinyl)-phenyl]acetamide or other salts thereof as API in a tablet. Furthermore, the surprising dispersion times obtained with tablets according to the invention are advantageous for swallowable tablets. In a further embodiment, the tablets according to the invention can be presented for dispersion in water. In respect of the stated above, the person skilled in the art understands that the dissolution behavior may be directly linked to resultant bioavailability properties of an API in vivo. Accordingly, a high degree of absolute bioavailability may be expected based on the dissolution properties of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate in a tablet of the invention.

Accordingly, the present invention, surprisingly und unexpectedly, provides for chemically stable, orally administrable pharmaceutical compositions of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate having PSD, PSR and SSA as defined herein, characterized by an absolute bioavailability of the resultant free base form of N-[5-(aminosulfonyl)-4-methyl-1,3-thiazol-2-yl]-N-methyl-2-[4-(2-pyridinyl)-phenyl]acetamide of at least 40 to 90%, preferably 50 to 90%, more preferably 60 to 85%, when administered in a pharmaceutical composition of the invention.

In yet another aspect the present invention, surprisingly und unexpectedly, provides for chemically stable, orally administrable pharmaceutical compositions of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate having PSD, PSR and SSA as defined herein, characterized by absolute bioavailability of the resultant free base form of N-[5-(aminosulfonyl)-4-methyl-1,3-thiazol-2-yl]-N-methyl-2-[4-(2-pyridinyl)-phenyl]acetamide of >40%, preferably >50%, even more preferably >70%, most preferred >80%, utmost preferred >90%, when administered in a pharmaceutical composition of the invention.

In yet another aspect the present invention provides for pharmaceutical compositions as described herein, effective to achieve an absolute bioavailability of 70%±30% of the resultant free base form of N-[5-(aminosulfonyl)-4-methyl-1,3-thiazol-2-yl]-N-methyl-2-[4-(2-pyridinyl)-phenyl]acetamide, when administered as crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles having PSD, PSR and SSA as defined herein in a pharmaceutical composition containing at least 5 mg, preferably at least 10 mg, more preferably at least 20 mg, most preferred at least 25 mg thereof.

In yet another aspect of the invention said absolute bioavailability of 70%±30% of the resultant free base form of N-[5-(aminosulfonyl)-4-methyl-1,3-thiazol-2-yl]-N-methyl-2-[4-(2-pyridinyl)-phenyl]acetamide is achieved in a human.

In the context of the present invention the term "bioavailability" denotes a subcategory of absorption. Bioavailability denotes the fraction of an administered oral dose of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate of the invention that reaches the systemic circulation of a subject as the resultant free base form of N-[5-(aminosulfonyl)-4-methyl-1,3-thiazol-2-yl]-N-methyl-2-[4-(2-pyridinyl)-phenyl]acetamide.

By definition, when a medication is administered intravenously, its bioavailability is 100%. However, when a medication is administered via other routes (such as orally), its bioavailability generally decreases (due to incomplete absorption and first-pass metabolism) or may vary from individual to individual. Bioavailability is one of the essential tools in pharmacokinetics, as bioavailability must be considered when calculating dosages for non-intravenous routes of administration.

The crystalline mono mesylate monohydrate salt of N-[5-(aminosulfonyl)-4-methyl-1,3-thiazol-2-yl]-N-methyl-2-[4-(2-pyridinyl)phenyl]acetamide, wherein the PSR, PSD and SSA is as defined herein, exhibits increased long term stability properties and a desired release kinetic and long term stability from pharmaceutical compositions, which is superior to other salts of N-[5-(aminosulfonyl)-4-methyl-1,3-thiazol-2-yl]-N-methyl-2-[4-(2-pyridinyl)phenyl]acetamide, which are known in the state of the art including also other mesylate salts.

As evident from FIG. 4 which shows the single-crystal X-ray structure analysis of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate, the salt is formed between the mesylate and the protonated pyridinyl ring. Moreover, exactly one mol equivalent methanesulfonic acid and one mol equivalent water is incorporated into the crystal structure, wherein the hydrogen atoms of the water molecule form hydrogen bridges with oxygen atoms of two different mesylate molecules.

Preferred conditions for the crystallization of N-[5-(aminosulfonyl)-4-methyl-1,3-thiazol-2-yl]-N-methyl-2-[4-(2-pyridinyl)-phenyl]acetamide mono methanesulfonic acid monohydrate are reflected by the preparation of a suspension of the free base in about 10 vol. (vol.=L/kg of free base) ethanol/water (1:1), adding 1.15 equivalents of methanesulfonic acid at 50-55° C. in less than 15 min, seeding with 0.5 mol % of final product, ageing for 1-1.5 h at 50° C. and cooling to 20-25° C. during 2.5 h. After further stirring for 1 h, the final product can be isolated by filtration and drying in vacuo, resulting in a yield of >95%. Using this procedure, crystalline N-[5-(amino-sulfonyl)-4-methyl-1,3-thiazol-2-yl]-N-methyl-2-[4-(2-pyridinyl)-phenyl]acetamide mono methanesulfonic acid monohydrate having the PSR, PSD and SSA as defined herein, and preferably having a particle size range of from 2 to 400 μm, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, in purity of >99% containing <2 ppm residual Pd could be prepared reproducibly concerning yield, purity, polymorphic form, PSD, PSR and SSA from a supersaturated solution of N-[5-(aminosulfonyl)-4-methyl-1,3-thiazol-2-yl]-N-methyl-2-[4-(2-pyridinyl)-phenyl]acetamide by crystallization under controlled conditions as described below.

Spontaneous crystallization from an over-saturated solution results in a co-precipitation of the free base. To simulate this process, a sample of N-[5-(amino-sulfonyl)-4-methyl-1,3-thiazol-2-yl]-N-methyl-2-[4-(2-pyridinyl)phenyl]acetamide mono methanesulfonic acid monohydrate was dissolved in a mixture of ethanol and water (1:1) at 50° C. and then cooled down and stirred at 0° C. for ca. 5 h. Samples of the precipitate were taken for microscopy exhibiting mainly small needles (see FIG. 3A) in contrast to the mono mesylate monohydrate, which crystallizes as prisms (see FIG. 3B). By investigating isolated needles applying $^1H$ NMR (nuclear magnetic resonance) no mono mesylate monohydrate could be detected, thus exhibiting the existence of mainly free base form. Keeping a suspension of this precipitate at 0° C. or at room temperature shows slow growth of the prisms consuming the needles (see FIG. 3C), which argues for a very slow conversion to the mesylate salt form. This experiment demonstrates the importance of selection of well-defined crystallization conditions.

To obtain N-[5-(amino-sulfonyl)-4-methyl-1,3-thiazol-2-yl]-N-methyl-2-[4-(2-pyridinyl)phenyl]acetamide mono methanesulfonic acid monohydrate in the desired PSD, PSR and SSA, also moderate to slow stirring of this mixture and a flat cooling ramp of this mixture to room temperature are preferred. Furthermore, it is preferred to add the methanesulfonic acid over 5-15 minutes at elevated temperature and to keep the resulting mixture at this elevated temperature for 1 to 2 hours after completion of the addition of methanesulfonic acid. The cooling to room temperature is performed within 2 to 3 hours and the mixture is thereafter slowly stirred for another hour at room temperature. Then the crystals are filtered off, washed with alcohol/water and dried under vacuum at a temperature between 20° C. and 60° C., preferably starting at 20° C. and ending at 60° C.

A modified way to obtain N-[5-(amino-sulfonyl)-4-methyl-1,3-thiazol-2-yl]-N-methyl-2-[4-(2-pyridinyl)phenyl]acetamide mono methanesulfonic acid monohydrate in the desired PSD, PSR and SSA applies the following conditions for the crystallization. Methanesulfonic acid is added at elevated temperatures, and preferably between 30° C. and 90° C., more preferably between 35° C. and 80° C., still more preferably between 40° C. and 70° C., still more preferably between 45° C. and 60° C. and most preferably at 50° C.-55° C. to the mixture of an organic solvent and water containing N-[5-(aminosulfonyl)-4-methyl-1,3-thiazol-2-yl]-N-methyl-2-[4-(2-pyridinyl)phenyl]-acetamide yielding a supersaturated solution of the mono mesylate monohydrate of N-[5-(aminosulfonyl)-4-methyl-1,3-thiazol-2-yl]-N-methyl-2-[4-(2-pyridinyl)phenyl]acetamide. Organic solvents which are miscible or consolute with water are preferred such as MeOH, EtOH, n-PrOH, I-PrOH, acetonitrile, THF, acetone. Moreover it is preferred to add seed crystals of N-[5-(aminosulfonyl)-4-methyl-1,3-thiazol-2-yl]-N-methyl-2-[4-(2-pyridinyl)phenyl]acetamide mono methane-sulfonic acid monohydrate to this supersaturated mixture also at elevated temperatures like 30° C. to 90° C., preferably 35° C. to 80° C., more preferably 40° C. to 70° C., still more preferably 45° C. to 60° C. and most preferably at 50° C.-55° C. Also moderate to slow stirring of this mixture and a slow cooling of this mixture to room temperature is preferred. Furthermore, it is preferred to add the methanesulfonic acid over 5 to 15 minutes at the elevated temperature and to keep the resulting mixture at this elevated temperature for 0.5 to 5 hour and more preferably for 1 to 2 hours after completion of the addition of the methanesulfonic acid. The cooling to room temperature is performed within 1 to 5 hour and preferably 2 to 3 hours and the mixture is thereafter slowly stirred for preferably another hour at room temperature. Then the crystals are filtered off, washed with alcohol/water and preferably dried under vacuum at a temperature between 20° C. and 60° C., preferably starting at 20° C. and ending at 60° C.

The crystalline N-[5-(aminosulfonyl)-4-methyl-1,3-thiazol-2-yl]-N-methyl-2-[4-(2-pyridinyl)-phenyl]acetamide mono methanesulfonic acid monohydrate with the PSD, PSR and SSA as defined herein, exhibits optimized release kinetics from pharmaceutical compositions and improved bioavailability. Furthermore, storage properties, especially the long-term stability of the API as well as of the pharmaceutical formulations are excellent.

X-ray powder diffraction spectra of film coated tablets (strengths 5 mg, 25 mg, 100 mg, powdered for measurement in comparison to placebo) after 24 months at room temperature revealed no change in crystallinity (see FIGS. 5 to 7).

Compared to the mesylate salt of N-[5-(aminosulfonyl)-4-methyl-1,3-thiazol-2-yl]-N-methyl-2-[4-(2-pyridinyl)phenyl]acetamide, the monohydrate of the mono mesylate salt of N-[5-(aminosulfonyl)-4-methyl-1,3-thiazol-2-yl]-N-methyl-2-[4-(2-pyridinyl)-phenyl]acetamide, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 1.0 $m^2/g$, preferably less than 0.6 $m^2/g$, and most preferably less than 0.3 $m^2/g$, surprisingly and unexpectedly has a greater thermostability of up to 170° C. A clear advantage of the N-[5-(aminosulfonyl)-4-methyl-1,3-thiazol-2-yl]-N-methyl-2-[4-(2-pyridinyl)phenyl]acetamide mono mesylate monohydrate, wherein the PSD, PSR and SSA are as defined herein, is its proven long-term stability. Therefore, the inventive N-[5-(aminosulfonyl)-4-methyl-1,3-thiazol-2-yl]-N-methyl-2-[4-(2-pyridinyl)-phenyl]acetamide mono mesylate monohydrate, which is characterized by the PSD, PSR and SSA as disclosed herein, is better suited for the preparation of long-term stable tablets compared to the free base form of N-[5-(aminosulfonyl)-4-methyl-1,3-thiazol-2-yl]-N-methyl-2-[4-(2-pyridinyl)phenyl]acetamide.

The crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to the invention is a useful compound for treatment and/or prophylaxis of infectious diseases and/or prevention of transmission of infectious diseases.

The crystalline N-[5-(aminosulfonyl)-4-methyl-1,3-thiazol-2-yl]-N-methyl-2-[4-(2-pyridinyl)-phenyl]acetamide mono methanesulfonic acid monohydrate is highly active against herpesviruses and infections caused by herpesviruses and/or transmission of a herpes virus or herpesviruses. Therefore, the inventive crystalline N-[5-(aminosulfonyl)-4-methyl-1,3-thiazol-2-yl]-N-methyl-2-[4-(2-pyridinyl)-phenyl]acetamide mono methanesulfonic acid monohydrate is especially useful for the preparation of a pharmaceutical composition for the treatment and/or prophylaxis of diseases, which are caused by herpesviruses or caused by the transmission of a herpes virus or herpesviruses.

The inventive mono mesylate monohydrate salt is especially useful for the treatment and/or prophylaxis of infections, which are caused by herpes simplex viruses, or for the prevention of transmission of a herpes virus or herpes viruses. Infections with herpes simplex viruses (HSV, subtype 1 and 2) are categorized into one of several distinct disorders based on the site of infection. Orofacial herpes simplex infection, the visible symptoms of which are colloquially called cold sores or fever blisters, affects the face and mouth. Orofacial herpes is the most common form of infection. Genital herpes is the second common form of a herpes simplex infection. Although genital herpes is largely believed to be caused by HSV-2 only, genital HSV-1 infections are increasing. Other disorders such as herpetic whitlow, herpes gladiatorum, ocular herpes (keratitis), cerebral herpes infection encephalitis, Mollaret's meningitis, neonatal herpes, and possibly Bell's palsy are also caused by herpes simplex viruses.

The inventive mono mesylate monohydrate salt is thus useful for the treatment and/or prophylaxis of infections, which are caused by herpes simplex viruses and/or for the prevention of transmission of herpes simplex viruses.

The mono mesylate monohydrate salt of the present invention can be combined and administered together with an anti-inflammatory agent such as acetylsalicylic acid and acetaminophen. Thus, combinations of the inventive mono mesylate monohydrate with acetylsalicylic acid and/or acetaminophen as well as pharmaceutical compositions containing such a combination are preferred.

Furthermore, the inventive mono mesylate monohydrate can be combined and can be used in combination with an anti-viral agent. The anti-viral agent is preferably an antimetabolite and most preferably a nucleobase analogue, nucleotide analogue or nucleoside analogue drug. It is further preferred if the anti-viral agent is useful against herpesviruses and/or against transmission of a herpes virus or herpes viruses and is selected from the group of drugs comprising but not limited to or consisting of: trifluridine, idoxuridine, foscarnet, cidofovir, ganciclovir, aciclovir or penciclovir or the respective prodrugs valaciclovir, famciclovir or valganciclovir.

The combination of the inventive mono mesylate monohydrate and a further active agent like an anti-inflammatory, immunomodulatory, or anti-viral agent, such as therapeutic vaccines, siRNAs, antisense oligonucleotides, nanoparticles or virus-uptake inhibitors such as n-docosanol, may be administered simultaneously in one single pharmaceutical composition or in more than one pharmaceutical composition, wherein each composition comprises at least one active agent.

The pharmaceutical compositions of the present invention can be prepared in a conventional solid and a conventional pharmaceutically-made adjuvant at suitable dosage level in a known way. Preferred preparations may be adapted for oral application. These administration forms include, for example, pills, tablets, film tablets, coated tablets, sustained release formulations, and capsules.

The pharmaceutical compositions according to the invention preferably comprise 5 to 70% by weight more preferably 10 to 30% by weight crystalline N-[5-(aminosulfonyl)-4-methyl-1,3-thiazol-2-yl]-N-methyl-2-[4-(2-pyridinyl)-phenyl]acet-amide mono methanesulfonic acid monohydrate (all percentage data are percentages by weight based on the weight of the pharmaceutical preparation), wherein the PSD, PSR and SSA is as defined herein. The pharmaceutical composition comprises usually 2 to 600 mg of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, preferably 5 to 500 mg, more preferably 10 to 300 mg and particularly preferably 20 to 200 mg, wherein PSD, PSR and SSA is as disclosed above.

The pharmaceutical composition according to the invention optionally comprises one or more filler, which, for example, are selected from the group consisting of: microcrystalline cellulose, fiber cellulose, calcium phosphates and mannitol Preferably, according to the invention, microcrystalline cellulose and mannitol are used. The pharmaceutical composition expediently comprises 20 to 80%, preferably 40 to 80%, particularly preferably 45 to 70% microcrystalline cellulose and 1 to 40%, preferably 5 to 30%, particularly preferably 10 to 20% mannitol. The pharmaceutical preparation according to the invention may comprise at least one disintegration auxiliary, which is, for example, selected from the group consisting of starch, pre-gelatinized starch, starch glycolates, cross-linked polyvinylpyrrolidone, sodium carboxymethylcellulose (=croscarmellose sodium) and other salts of carboxymethylcellulose. A mixture of two disintegration agents can also be used. According to the invention, the use of croscarmellose sodium is preferred. The pharmaceutical composition expediently comprises 3 to 35%, preferably 5 to 30% and particularly preferably 5 to 10% of the disintegration auxiliary(ies). The pharmaceutical composition of the invention may comprise at least one lubricant selected from the group consisting of fatty acids and their salts. According to the invention, the use of magnesium stearate is particularly preferred.

The pharmaceutical composition of the invention may comprise a flow agent, which could be colloidas anhydrous silica or talcum powder. According to the invention, the use of colloidas anhydrous silica is particularly preferred. The flow agent is expediently used in an amount of 0.3 to 2.0%, particularly preferably from 0.4 to 1.5% and most preferably from 0.5 to 1%.

A particularly preferred pharmaceutical composition of the invention comprises: 5%-30% crystalline N-[5-(aminosulfonyl)-4-methyl-1,3-thiazol-2-yl]-N-methyl-2-[4-(2-pyridinyl)phenyl]acetamide mono methanesulfonic acid monohydrate, wherein the PSD, PSR and SSA is as defined herein and preferably the particle size distribution is defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm , d(0.5) from 100 to 175 μm, d(0.9) from 200 to 350 μm with a specific surface area of the particles less than 0.3 $m^2/g$, 5%-10% croscarmellose-sodium, 0.5 to 0.7% magnesium stearate, 40%-70% microcrystalline cellulose, 10%-20% mannitol and 0.5% to 1% colloidal anhydrous silica.

Further pharmaceutical compositions according to the invention preferably comprise 30 to 90% more preferably 50 to 70% by weight crystalline N-[5-(aminosulfonyl)-4-methyl-1,3-thiazol-2-yl]-N-methyl-2-[4-(2-pyridinyl)-phenyl]acet-amide mono methanesulfonic acid monohydrate, wherein the PSD, PSR and SSA is as defined herein and preferably the particle size distribution is defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ (all percentage data are percentages by weight based on the weight of the pharmaceutical preparations). The pharmaceutical composition comprises usually 20 to 750 mg as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein the PSD, PSR and SSA is as defined herein and preferably 50 to 500 mg as free base equivalent and particularly preferably 50 to 250 mg as free base equivalent based on a single dosage.

As used herein for the specification and the claims, the given mg-dosages for the crystalline N-[5-(aminosulfonyl)-4-methyl-1,3-thiazol-2-yl]-N-methyl-2-[4-(2-pyridinyl)-phenyl]acetamide mono methanesulfonic acid monohydrate as API in a pharmaceutical composition of the invention, particularly for tablet formulations are ever described as the free base equivalent dosage, which means that the content of crystalline N-[5-(aminosulfonyl)-4-methyl-1,3-thiazol-2-yl]-N-methyl-2-[4-(2-pyridinyl)-phenyl]acetamide mono methanesulfonic acid monohydrate is approximately 1.3 times higher as indicated. This is due to the fact that the pharmacologically active form in vivo is the free base form of N-[5-(aminosulfonyl)-4-methyl-1,3-thiazol-2-yl]-N-methyl-2-[4-(2-pyridinyl)-phenyl]acetamide, which is however administered as the mono mesylate monohydrate salt form having the characteristic PSD, PSR and SSA of the invention.

Therefore, the term "free base equivalent" as used herein and in the claims denotes the dosage of the pharmacologically active form, thus calculated as free base form of N-[5-(aminosulfonyl)-4-methyl-1,3-thiazol-2-yl]-N-methyl-2-[4-(2-pyridinyl)-phenyl]acetamide.

The pharmaceutical composition according to the invention optionally comprises one or more dry binders, which, for example, are selected from the group consisting of microcrystalline cellulose, fiber cellulose, calcium phosphates, and mannitol. Preferably, microcrystalline cellulose is used. This is commercially available under the designation AvicelB, for example. The pharmaceutical composition expediently comprises 1 to 20%, preferably 1 to 10%, particularly preferably 1 to 5% of the dry binder(s). The pharmaceutical preparation according to the invention may comprise at least one disintegration auxiliary which is for example selected from the group consisting of starch, pre-gelatinized starch, starch glycolates, cross-linked polyvinylpyrrolidone, sodium carboxymethylcellulose (=croscarmellose sodium) and other salts of carboxymethylcellulose. A mixture of two disintegration agents can also be used. The use of croscarmellose sodium and cross-linked polyvinylpyrrolidone or a mixture of the two is preferred. The pharmaceutical composition expediently comprises 3 to 35%, preferably 10 to 30% and particularly preferably 15 to 25% of the disintegration auxiliary(ies). The pharmaceutical preparation of the invention may comprise at least one lubricant selected from the group consisting of fatty acids and their salts. The use of magnesium stearate is particularly preferred.

A pharmaceutical composition for a tablet with 25 mg of the active pharmacologic ingredient (calculated as free base form) comprises 32.3 mg of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein the PSD, PSR and SSA is as defined herein and preferably the particle size distribution is defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, 60.9 mg of microcrystalline cellulose, 9.8 mg of croscarmellose sodium, 20.0 mg of mannitol, 1.3 mg of colloidal anhydrous silica, and 0.9 mg of magnesium stearate. The total weight of the blend is 125.0 mg.

A further pharmaceutical composition for a tablet with 100 mg of the active pharmacologic ingredient (calculated as free base form) comprises 129.0 mg of the inventive crystalline N-[5-(aminosulfonyl)-4-methyl-1,3-thiazol-2-yl]-N-methyl-2-[4-(2-pyridinyl)-phenyl]acet-amide mono methanesulfonic acid monohydrate, 243.4 mg of microcrystalline cellulose, 39.0 mg of croscarmellose sodium, 80.1 mg of mannitol, 5.0 mg of colloidal anhydrous silica, and 3.5 mg of magnesium stearate. The total weight of the blend is 500.0 mg.

Furthermore, the present invention also includes pharmaceutical compositions for sublingual application, which preparations in addition to typical vehicles contain at least crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein the PSD, PSR and SSA is as defined herein, as active ingredient.

An inventive pharmaceutical composition may contain the following preservatives: phenoxyethanol, formaldehyde solution, parabens, pentanediol, or sorbic acid.

As pharmaceutically acceptable carrier, excipient and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscarmellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

The following examples are included to demonstrate preferred embodiments of the invention. It should be appreciated by those of skill in the art that the techniques disclosed in the examples, which follow, represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The pharmaceutical compositions according to the invention can be administered to a patient in need thereof at a once daily dose of about 20 to 750 mg as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein the PSD, PSR and SSA is as defined herein and preferably the particle size distribution is defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, preferably of about 50 to 500 mg as free base equivalent and even more preferably of about 50 to 250 mg as free base equivalent based on a single dosage. The pharmaceutical compositions according to the invention can also be administered to a patient in need thereof thrice daily, twice daily, once daily, thrice weekly, twice weekly, or once weekly. The administration on a thrice weekly, twice weekly, or once weekly basis is preferred and especially preferred is a once weekly administration, i.e. an administration one time a week of a pharmaceutical composition containing between 400 mg to 500 mg as free base equivalent of the inventive N-[5-(aminosulfonyl)-4-methyl-1,3-thiazol-2-yl]-N-methyl-2-[4-(2-pyridinyl)-phenyl]acet-amide mono methanesulfonic acid monohydrate. Moreover it is preferred to start the administration of the mono mesylate monohydrate of the present invention with a high loading dose, for instance, with an initial single dose of 400 mg to 800 mg as free base equivalent and to continue the administration with a lower dose of 100 mg to 150 mg as free base equivalent per day or per week over the period of treatment.

Particularly, the definite crystalline mono mesylate monohydrate salt of N-[5-(aminosulfonyl)-4-methyl-1,3-thiazol-2-yl]-N-methyl-2-[4-(2-pyridinyl)-phenyl]acetamide with the characteristic PSR, PSD and SSA as disclosed herein exhibits characteristic PK/PD profiles in vivo as the free base form when administered in a pharmaceutical composition in accordance with the invention.

Exposure of the free base form of N-[5-(aminosulfonyl)-4-methyl-1,3-thiazol-2-yl]-N-methyl-2-[4-(2-pyridinyl)-phenyl]acetamide to the human body may be measured by high pressure liquid chromatography (HPLC) by looking at different pharmacokinetic parameters in suitable bodily fluids such as for instance blood plasma and urine, the most common parameters being the $C_{max}$, the so-called area under the curve (AUC), and the terminal half-life ($t_{1/2z}$). Hereto, the person skilled in the art understands that said parameters are determined by using adequate bioanalytical methods with adequate sensitivity, specificity, ruggedness, stability and repeatability, as for instance a qualified liquid chromatography triple quad mass spectrometry based method coupled with a suitable extraction method for the separation of the analyte from, e.g. the blood plasma. For example, AUC values may be calculated from 0-24 hours using the trapezoid method.

For instance, after administration of crystalline mono mesylate monohydrate salt of N-[5-(aminosulfonyl)-4-methyl-1,3-thiazol-2-yl]-N-methyl-2-[4-(2-pyridinyl)phenyl]-acetamide, its concentration in the blood increases in the form of the free base of N-[5-(aminosulfonyl)-4-methyl-1,3-thiazol-2-yl]-N-methyl-2-[4-(2-pyridinyl)phenyl]-acetamide until it reaches a peak concentration, which measured in blood by a suitable HPLC method is the $C_{max}$ and the time taken to reach the $C_{max}$, is termed $t_{max}$. The area under the blood plasma concentration curve (area under the curve abbreviated as AUC) is another useful measurement and represents the drug exposure of the free base in the systemic circulation over a period of time; e.g. 0-24 h or 0-∞.

The mean $C_{max}$, values are derived from averaging the highest observed free base concentration of N-[5-(aminosulfonyl)-4-methyl-1,3-thiazol-2-yl]-N-methyl-2-[4-(2-pyridinyl)phenyl]acetamide for all members of a subject group under investigation.

The mean $C_{max,ss}$ values are derived from averaging the highest observed free base concentration at steady state of N-[5-(aminosulfonyl)-4-methyl-1,3-thiazol-2-yl]-N-methyl-2-[4-(2-pyridinyl)phenyl]acetamide for all members of a subject group under investigation.

In a specific aspect the present invention provides for a pharmaceutical composition as described above for the crystalline mono mesylate monohydrate salt of N-[5-(aminosulfonyl)-4-methyl-1,3-thiazol-2-yl]-N-methyl-2-[4-(2-pyridinyl)-phenyl]acetamide, effective to achieve a mean maximum blood plasma concentration (mean $C_{max}$) of the free base of N-[5-(aminosulfonyl)-4-methyl-1,3-thiazol-2-yl]-N-methyl-2-[4-(2-pyridinyl)-phenyl]acetamide in a subject of at least one of a) 608±184 ng/ml for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

b) 1306±125 ng/ml for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

c) 2613±1341 ng/ml for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

d) 3600±752 ng/ml for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

e) 4648±1813 ng/ml for a 320 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

f) 6926±1656 ng/ml for a 400 mg dosage as free base equivalent of crystalline N-[5-(aminosulfonyl)-4methyl-1,3-thiazol-2-yl]-N-methyl-2-[4-(2-pyridinyl)-phenyl]acetamide mono methanesulfonic acid monohydrate, said dosage being a single oral dose administered;

g) 6921±2190 ng/ml for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered.

In yet another specific aspect the present invention provides for a pharmaceutical composition as described above for the crystalline mono mesylate monohydrate salt of N-[5-(aminosulfonyl)-4-methyl-1,3-thiazol-2-yl]-N-methyl-2-[4-(2-pyridinyl)-phenyl]acetamide, effective to achieve a mean maximum blood plasma concentration (mean $C_{max}$) of the free base of N-[5-(aminosulfonyl)-4-methyl-1,3-thiazol-2-yl]-N-methyl-2-[4-(2-pyridinyl)-phenyl] in a subject of at least one of a) 608±184 ng/ml for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 10090±3114 ng-h/ml in a subject for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 72±3 h on average; said dosage being a single oral dose administered;

b) 1306±125 ng/ml for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 21940±2057 ng-h/ml in a subject for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 74±5 h on average; said dosage being a single oral dose administered;

c) 2613±1341 ng/ml for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to a achieve an $AUC_{0-24h}$ of 40470±16700 ng-h/ml in a subject for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 63±6 h on average; said dosage being a single oral dose administered;

d) 3600±752 ng/ml for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 59610±12770 ng-h/ml in a subject for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 64±5 h on average; said dosage being a single oral dose administered;

e) 4648±1813 ng/ml for a 320 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 76250±27630 ng-h/ml in a subject for a 320 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 57±3 h on average; said dosage being a single oral dose administered;

f) 6926±1656 ng/ml for a 400 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 104800±25740 ng-h/ml in a subject for a 400 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 57±4 h on average; said dosage being a single oral dose administered;

g) 6921±2190 ng/ml for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 112800±34260 ng-h/ml in a subject for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 53±4 h on average; said dosage being a single oral dose administered.

In yet another specific aspect the present invention provides for a pharmaceutical composition as described above for the crystalline mono mesylate monohydrate salt of N-[5-(aminosulfonyl)-4-methyl-1,3-thiazol-2-yl]-N-methyl-2-[4-(2-pyridinyl)-phenyl]acetamide, effective to achieve a mean maximum blood plasma concentration at steady state (mean $C_{max,ss}$) of the free base of N-[5-(aminosulfonyl)-4-methyl-1,3-thiazol-2-yl]-N-methyl-2-[4-(2-pyridinyl)-phenyl]acetamide in a subject of at least one of a) 1358±167 ng/ml for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a steady state dose achieved after once daily single doses administered for 21 days;

b) 6358±1701 ng/ml for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a steady state dose achieved after once daily single doses administered for 21 days;

c) 9987±2608 ng/ml for a 200 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a steady state dose achieved after once daily single doses administered for 21 days.

In yet another specific aspect the present invention provides for a pharmaceutical composition as described above for the crystalline mono mesylate monohydrate salt of N-[5-(aminosulfonyl)-4-methyl-1,3-thiazol-2-yl]-N-methyl-2-[4-(2-pyridinyl)-phenyl]acetamide, effective to achieve a mean maximum blood plasma concentration at steady state (mean $C_{max,ss}$) of the free base of N-[5-(aminosulfonyl)-4-methyl-1,3-thiazol-2-yl]-N-methyl-2-[4-(2-pyridinyl)-phenyl]acetamide in a subject of at least one of a) 1358±167 ng/ml for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{tss}$ of 23430±3020 ng-h/ml in a subject for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 69±6 h on average, said dosage being a steady state dose achieved after once daily single doses administered for 21 days;

b) 6358±1701 ng/ml for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{t,ss}$ of 108800±28610 ng-h/ml in a subject for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 60±4 h on average, said dosage being a steady state dose achieved after once daily single doses administered for 21 days;

c) 9987±2608 ng/ml for a 200 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{t,ss}$ of 168500±37970 ng-h/ml in a subject for a 200 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 57.19±5.451 h on average, said dosage being a steady state dose achieved after once daily single doses administered for 21 days.

In yet another specific aspect the present invention provides for a method of treatment and/or prophylaxis of an infectious disease and/or prevention of transmission of an infectious disease wherein a mean maximum blood plasma concentration (mean $C_{max}$) of the free base of N-[5-(aminosulfonyl)-4-methyl-1,3-thiazol-2-yl]-N-methyl-2-[4-(2-pyridinyl)-phenyl]acetamide of at least one of a) 608±184 ng/ml for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{0-24h}$ of 10090±3114 ng-h/ml for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 72±3 h on average;

b) 1306±125 ng/ml for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{0-24h}$ of 21940±2057 ng-h/ml for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 74±5 h on average;

c) 2613±1341 ng/ml for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{0-24h}$ of 40470±16700 ng-h/ml for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 63±6 h on average;

d) 3600±752 ng/ml for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{0-24h}$ of 59610±12770 ng-h/ml for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 64±5 h on average;

e) 4648±1813 ng/ml for a 320 mg dosage as free base equivalent of crystalline N-[5-(aminosulfonyl)-4methyl-1,3-thiazol-2-yl]-N-methyl-2-[4-(2-pyridinyl)-phenyl]acetamide mono methanesulfonic acid monohydrate and/or an $AUC_{0\text{-}24h}$ of 76250±27630 ng-h/ml for a 320 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 57±3 h on average;

f) 6926±1656 ng/ml for a 400 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{0\text{-}24h}$ of 104800±25740 ng-h/ml for a 400 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 57±4 h on average;

g) 6921±2190 ng/ml for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{0\text{-}24h}$ of 112800±34260 ng-h/ml for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 53±4 h on average, is achieved in a human; and wherein said dosage is a single oral dose administered.

In yet another specific aspect the present invention provides for a method of treatment and/or prophylaxis of an infectious disease and/or prevention of transmission of an infectious disease wherein a mean maximum blood plasma concentration at steady state (mean $C_{max,ss}$) of the free base of N-[5-(aminosulfonyl)-4-methyl-1,3-thiazol-2-yl]-N-methyl-2-[4-(2-pyridinyl)-phenyl]acetamide of at least one of a) 1358±167 ng/ml for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{t,ss}$ of 23430±3020 ng-h/ml for a 25 mg dosage as free base equivalent of crystalline N-[5-(aminosulfonyl)-4-methyl-1,3-thiazol-2-yl]-N-methyl-2[4-(2-pyridinyl)-phenyl]acetamide mono methanesulfonic acid monohydrate, wherein $t_{1/2z}$ is 69±6 h on average;

b) 6358±1701 ng/ml for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or an $AUC_{t,ss}$ of 108800±28610 ng-h/ml in a subject for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, wherein $t_{1/2z}$ is 60±4 h on average;

c) 9987±2608 ng/ml for a 200 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{t,ss}$ of 168500±37970 ng-h/ml in a subject for a 200 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 57.19±5.451 hon average, is achieved in a human; and wherein said dosage is a steady state dose achieved after once daily single doses administered for 21 days.

In yet another specific aspect of the invention said mean maximum blood plasma concentration (mean $C_{max}$) of the free base of N-[5-(aminosulfonyl)-4-methyl-1,3-thiazol-2-yl]-N-methyl-2-[4-(2-pyridinyl)-phenyl]acetamide is achieved in a human.

In yet another specific aspect of the invention said mean maximum blood plasma concentration at steady state (mean $C_{max,ss}$) of the free base of N-[5-(aminosulfonyl)-4-methyl-1,3-thiazol-2-yl]-N-methyl-2-[4-(2-pyridinyl)-phenyl]acetamide is achieved in a human.

In yet another specific aspect of the invention said $AUC_{0\text{-}24h}$, $AUC_{0\text{-}\infty}$ and $t_{1/2z}$ is achieved in a human.

In yet another specific aspect of the invention said $AUC_{t,ss}$ and $t_{1/2z}$ is achieved in a human.

As used in the specification and the claims "$AUC_{t,ss}$" denotes the area under the analyte versus time concentration curve over a dosing interval (tau) at steady-state (ss), calculated by linear up/log down summation.

As used in the specification, the general expression "$AUC_{t1\text{-}t2}$" denotes the area under the analyte versus time concentration curve from point in time $t_1$ to point in time $t_2$, calculated by linear up/log down summation. For example $AUC_{0\text{-}24}$ denotes the area under the analyte versus time concentration curve from point in time of administration ($t_1$=0) to the point in time of 24 h after administration ($t_2$=24h). Accordingly, $AUC_{0\text{-}\infty}$ denotes the concentration from time of administration up to infinity, calculated as $$AUC_{0-\infty} = AUC_{0-last} + \frac{C_{last}}{\lambda_z},$$

wherein $AUC_{0\text{-}last}$ is defined as the area under the analyte vs. time concentration up to time of the last qualifiable concentration, calculated by linear up/log down summation and $C_{last}$ is defined as last quantifiable observed analyte concentration. $\lambda_z$ is the apparent terminal elimination rate constant, determined by linear regression of terminal points of In-linear analyte concentration-time curve.

$C_{max}$ is the maximal observed analyte concentration and $t_{max}$ is the time to reach $C_{max}$; $t_{1/2z}$ is defined as the apparent terminal elimination half-life, calculated as $$t_{1/2z} = \frac{\ln(2)}{\lambda_z},$$

wherein $\lambda_z$ is defined as above.

As used in the specification and the claims "$t_{1/2z}$" denotes the apparent terminal elimination half-life calculated as: $t_{1/2z}=0.693/\lambda_z$ Thereby, $\lambda_z$ denotes the apparent terminal elimination rate constant.

Further, it should be noted that the crystalline mono mesylate monohydrate salt of N-[5-(aminosulfonyl)-4-methyl-1,3-thiazol-2-yl]-N-methyl-2-[4-(2-pyridinyl)phenyl]-acetamide of the invention is used as API for tablet formulation in accordance with the invention, whereas the free base form of N-[5-(aminosulfonyl)-4-methyl-1,3-thiazol-2-yl]-N-methyl-2-[4-(2-pyridinyl)phenyl]-acetamide, having the formula

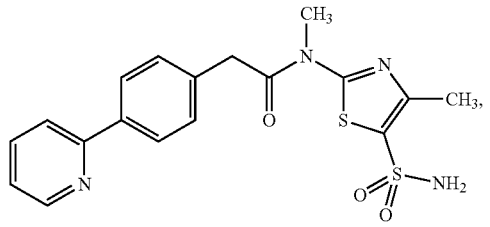

is the resultant pharmacologically active form in the body of a subject after administration of crystalline mono mesylate monohydrate salt of N-[5-(aminosulfonyl)-4-methyl-1,3-thiazol-2-yl]-N-methyl-2-[4-(2-pyridinyl)phenyl]-acetamide, preferably after oral administration thereof.

Further, the person skilled in the art understands that the pharmaceutical compositions of the invention among each other comprise physical or chemical dosage form characteristics, which may modulate either one of said mean $C_{max}$, $AUC_{0-24h}$, $AUC_{t,ss}$, $AUC_{0-\infty}$, and $t_{1/2z}$ as given in the above specific aspects of the invention.

Further, in accordance with the invention the person skilled in the art understands that food intake prior to administration of the crystalline mono mesylate monohydrate salt of N-[5-(aminosulfonyl)-4-methyl-1,3-thiazol-2-yl]-N-methyl-2-[4-(2-pyridinyl)phenyl]-acetamide of a subject may influence positively the in vivo PK/PD profile of the resultant free base of N-[5-(aminosulfonyl)-4-methyl-1,3-thiazol-2-yl]-N-methyl-2-[4-(2-pyridinyl)phenyl]-acetamide. Thus, in accordance with the invention a decreased absorption rate and a delayed $t_{max}$ of the resultant free base of N-[5-(aminosulfonyl)-4-methyl-1,3-thiazol-2-yl]-N-methyl-2-[4-(2-pyridinyl)phenyl]acetamide may be expected in fasted subjects after administration of crystalline mono mesylate monohydrate salt of N-[5-(aminosulfonyl)-4-methyl-1,3-thiazol-2-yl]-N-methyl-2-[4-(2-pyridinyl)phenyl]-acetamide.

By contrast, food intake prior to administration of crystalline mono mesylate monohydrate salt of N-[5-(aminosulfonyl)-4-methyl-1,3-thiazol-2-yl]-N-methyl-2-[4-(2-pyridinyl)phenyl]acetamide may lead to an increase in mean $C_{max}$ of at least about 25% and an increase in AUC of at least about 10% of the resultant free base of N-[5-(aminosulfonyl)-4-methyl-1,3-thiazol-2-yl]-N-methyl-2-[4-(2-pyridinyl)phenyl]-acetamide in human blood plasma when measured by suitable HPLC method. Thereby $t_{1/2z}$ remains constant.

In accordance with the invention, the administration of crystalline mono mesylate monohydrate salt of N-[5-(aminosulfonyl)-4-methyl-1,3-thiazol-2-yl]-N-methyl-2-[4-(2-pyridinyl)phenyl]-acetamide with the free base equivalent dosages as disclosed herein is safe and well tolerated by a subject in need thereof. No dose-dependent adverse events are to be expected when crystalline mono mesylate monohydrate salt of N-[5-(aminosulfonyl)-4-methyl-1,3-thiazol-2-yl]-N-methyl-2-[4-(2-pyridinyl)phenyl]-acetamide is administered as disclosed herein.

Further modifications and alternative embodiments of various aspects of the invention will be apparent to those skilled in the art in view of this description. Accordingly, this description is to be construed as mere illustrative and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Example 1: Synthesis of Crystalline N-[5-(aminosulfonyl)-4-methyl-1,3-thiazol-2-yl]-N-methyl-2-[4-(2-pyridinyl)-phenyl]acetamide Mono Methanesulfonic Acid Monohydrate Particles Having the Inventive PSD, PSR and SSA Step 1 (Suzuki-Miyaura Coupling and Saponification)

The inertized reactor is charged with bis(triphenylphosphine)palladium(II) chloride (0.010 eq.) and reinertized. Then, toluene (1.65 vol.) is added. After heating to 40° C., triethylamine (3.00 eq.) is added. A solution of ethyl-4-bromophenylacetate (1.00 eq.) in toluene (0.82 vol.) is added. The resulting suspension is heated to 90-95° C. prior 30 to dosing pinacol borane (1.30 eq.) over a period of 60-90 min. Stirring at 90-95° C. is continued for at least 2 more h before conversion is checked by HPLC. After cooling to 10° C., 2-chloropyridine (1.00 eq.) is charged to the reaction mixture. Then, 30% NaOH (6.00 eq.) is added followed by heating to 55-60° C. Stirring at this temperature is continued for at least 4 h before conversion is checked by HPLC. Once conversion is deemed complete, the reaction mixture is concentrated at about 300 mbar until 0.8 vol. (vol. refers to kg of starting material (=1.00 eq) in the respective step, i.e. L/kg starting material) of distillate have been collected. The reaction mixture is diluted with water (2.72 vol.), cooled to 20° C. and the phases are separated. The organic layer is discarded, while the pH of the aqueous layer is adjusted to pH 1 by addition of 33% HCl at 20° C. MIBK (2.30 vol.) and Celite (165 g/kg) are added and the resulting mixture is stirred for at least 15 min at 20° C. before the solids are removed by filtration. The reactor and the filter cake are rinsed successively with water and the combined filtrate is transferred back into the reactor. The phases are separated and the aqueous layer is washed twice more with MIBK. After dilution with water, the aqueous acidic product solution was heated to 55° C. and filtered through a plug packed with Celite at the bottom and activated charcoal on top. The Celite/charcoal plug was washed once more with pre-heated water (0.5 vol., 55° C.) and the combined filtrate was charged back into the reactor. At 20° C., the pH was adjusted to ~3.0 by addition of 30% NaOH before the product solution was heated to 60° C. More NaOH was dosed to adjust the pH to 4.1-4.3. The resulting suspension was stirred for 1-1.5 h at 60° C. prior to being cooled to 20° C. After additional stirring for at least 1 h at this temperature, the product was filtered, washed twice with water, pre-dried in a flow of $N_2$ and finally dried in vacuum at 50-65° C. Typical yield: 38-41%.

Step 2 (Amide Coupling)

The reactor is charged with product from step 1 (1.00 eq.) and 4-methyl-2-(methylamino)-1,3-thiazole-5-sulfonamide (1.02 eq.). THF (7.08 vol.) and NMP (1.11 vol.) are added. The resulting suspension is cooled to 0° C. prior to adding 1-ethyl-3-(3-dimethylaminopropyl)carbodiimide hydrochloride (1.23 eq.) in 4 equal portions over a period of >90 min. After at least 2 more h at 0° C., the reaction mixture is warmed to 20° C. At this temperature, stirring is continued for additional 2 h before conversion is checked by HPLC. Then, at 10-15° C. about 2% (0.2 vol.) of the reaction mixture are added to water (12.3 vol.) within at least 5 min. The resulting thin suspension is stirred at 10-15° C. for at least 1 h prior to dosage of the remaining bulk of the reaction mixture over >4 h. Stirring at 10-15° C. is continued for at least 0.5 h before the solids are filtered off, washed with water and dried on a nutsche filter in a steady flow of $N_2$ until deemed sufficiently dry (LOD<45% w/w; LOD: Loss on drying).

The feed reactor is charged with the crude product, THF (8.15 vol.), and water (up to 1.17 vol. depending on the loss on drying of crude product). The resulting suspension is heated to 60-65° C. and stirred for 1 h at this temperature. An almost clear solution is obtained which is subjected to polish filtration using a heatable lense filter heated to 60° C. The feed reactor, the transfer lines and the filter are successively rinsed with a mixture of THF (0.44 vol.) and purified water (0.06 vol.) at 60-65° C. The combined filtrate is collected in a separate reactor and heated to 50-55° C. To the reactor content, water (3.23 vol.) is dosed over at least 30 min. Stirring at 50-55° C. is continued for 1-1.5 h before another portion of water (8.93 vol.) is slowly added within 2 h. After stirring for 1-1.5 h at 50° C., the resulting suspension is cooled to 5° C. over 2.5 h and stirred for further 0.5 h. Then, the solids are filtered off, washed with water (3×2.96 vol.) and pre-dried on the nutsche filter in a steady flow of $N_2$. Final drying is accomplished in vacuo at 50-65° C. using a conical drier. Typical yield: 78-83%.

Step 3 (Salt Formation)

The reactor is charged with product from step 2 (1.00 eq.), ethanol (4.96 vol.) and water (4.96 vol.). After heating the resulting suspension to 50-55° C., methanesulfonic acid (1.15 eq.) is added within <15 min. Complete dissolution of starting materials is typically observed at the very end of addition. Immediately within the next 5 min, stirring is reduced to the minimum acceptable rate and the reaction mixture is seeded with N-[5-(aminosulfonyl)-4-methyl-1,3-thiazol-2-yl]-N-methyl-2-[4-(2-pyridinyl)-phenyl]acetamide mono methanesulfonic acid monohydrate (0.005 eq.) which was prepared in the desired polymorphic form in a preceding experiment. Slow stirring at 50-55° C. is continued for 60 to 90 min prior to cooling down to 20 to 25° C. during >2.5 h. After stirring for 1 more h, the solids are filtered off, washed with ethanol/water 5:2 V/V (3.10 vol.), pre-dried in a nitrogen flow and transferred into a conical drier for final drying in vacuo at 20 to 60° C. Typical yield: >95%.

Particle Analysis and Detection

Malvern Mastersizer 2000 with a dispersion unit Malvern Hydro 2000S was used for liquid dispersion. Dispersing agent was Span™ 80 used at a concentration of 0.1% (volume/volume) in n-heptane. Stirring rate was 2,500 rounds per minute. Typically, a slurry of 50 milligrams of N-[5-(aminosulfonyl)-4-methyl-1,3-thiazol-2-yl]-N-methyl-2-[4-(2-pyridinyl)phenyl]acetamide mono methanesulfonic acid monohydrate was prepared in a vial containing 4 to 5 mL dispersant. Should any agglomerates have occurred, then these were converted to primary particles by ultrasonic treatment for 10 seconds. Those with ordinary skills in the art may recognize that ultrasonic treatment is common practice in converting agglomerates to smaller particles. Once the suspension had been generated, the suspension was transferred to the Malvern Mastersizer 2000 with a dispersion unit Hydro 2000S by pipetting, until an optimal concentration range had been reached. The optimal concentration range was assessed by the obscuration value displayed by the Malvern Mastersizer 2000. Typically, optimal obscuration values are in the range from about 10 to about 20 percent. Then, the measurement was performed with automatic subtraction of the background. Data were analyzed automatically using the Fraunhofer diffraction equation. For microscopy, either the slurry used for particle size analysis or a new batch was used. The size of the observed particles was determined by means of the software analySIS start 5.0 (Olympus Soft Imaging Solutions GmbH). The procedure described above complies with USP 429 (light diffraction measurement of particle size) and Ph. Eur. 2.9.31 (particle size analysis by laser light diffraction). In addition to particle size analysis by laser light diffraction, an optical investigation using a microscope was conducted. In case of release measurements, system suitability testing must be performed prior to dispersing, which is common practice for those skilled in the art.

Example 2

The trials disclosed by example 2 were conducted in order to investigate the influence of the particle size distribution (PSD) of the API on the dissolution properties of the tablet cores.

The term "particle size distribution" of a powder, or granular material, or particles dispersed in fluid, as used within this application, is a list of values or a mathematical function that defines the relative amounts of particles present, sorted according to size. The d(0.1), d(0.5) and d(0.9) values indicate that 10%, 50% and 90% of the particles measured were less than or equal to the size stated. For 40 example, values of d(0.1)=52, d(0.5)=129 and d(0.9)=257 mean that 10% of the particles were less than or equal to 52 μm, 50% were less than or equal to 129 μm and 90% were less than or equal to 257 μm (cf. Table 1, trial batch number G05). In order to study the dissolution properties of the tablet cores with different PSD of the inventive N-[5-(aminosulfonyl)-4-methyl-1,3-thiazol-2-yl]-N-methyl-2-[4-(2-pyridinyl)-phenyl]acetamide mono methanesulfonic acid monohydrate, 100 mg and 25 mg (calculated as free base form; i.e. the free base equivalent thereof) tablet cores containing the inventive N-[5-(aminosulfonyl)-4-methyl-1,3-thiazol-2-yl]-N-methyl-2-[4-(2-pyridinyl)-phenyl]acetamide mono methanesulfonic acid monohydrate in an amount of 129 mg and 32.3 mg, respectively, were prepared.

Type and size of the tablet cores 100 mg tablet core, diameter 11 mm 25 mg tablet core, diameter 7 mm Equipments Blending: Bohle MC5 with glass tube Tabletting Kilian rotary press with chamber feed shoe Tooling 100 mg dose strength: 11r11 or 12r11 with break score on one site Tooling 25 mg dose strength: 7r6

Analytics

Dissolution (1000 ml, 0.1 M HCl, paddle apparatus according to USP apparatus 2, paddle speed 50 rounds per minute, n=6)

Compounds (API)

API: N-[5-(aminosulfonyl)-4-methyl-1,3-thiazol-2-yl]-N-methyl-2-[4-(2-pyridinyl)-phenyl]acet-amide mono methanesulfonic acid monohydrate, wherein at least 65 v/v % N-[5-(Aminosulfonyl)-4-methyl-1,3-thiazol-2-yl]-N-methyl-2-[4-(2-pyridinyl)-phenyl]-acetamide mono methanesulfonic acid monohydrate particles fall in a particle size range of from 2 to 500 micrometer (μm).

G01, G02, G03, G04, G05 are five different tablet test batches of the N-[5-(aminosulfonyl)-4-methyl-1,3-thiazol-2-yl]-N-methyl-2-[4-(2-pyridinyl)-phenyl]acet-amide mono methanesulfonic acid monohydrate, wherein the particle size is in a range from 1 to 400 μm with a particle size distribution of d(0.1), d(0.5) and d(0.9) shown by Table 1.

TABLE 1

Particle size distribution (PSD) of different batches of N-[5-(aminosulfonyl)-4-methyl-1,3-thiazol-2-yl]-N-methyl-2-[4-(2-pyridinyl)-phenyl]acetamide mono methanesulfonic acid monohydrate.

| API batch number | Trial batch number | Particle size distribution d(0.1) [μm] | d(0.5) [μm] | d(0.9) [μm] | Specific surface area [$m^2/g$] |
|---|---|---|---|---|---|
| BXR4FLS | G01 | 3 | 51 | 102 | 0.7 |
| BXR3NC1 | G02 | 43 | 118 | 254 | 0.1 |
| NE-023932-A-4-26 crude 1#1 M1 | G03 | 1 | 4 | 11 | 2.4 |
| NE-023932-A-4-27 IPC 1#1 | G04 | 22 | 66 | 143 | 0.2 |
| NE-023932-batch-02-2010 | G05 | 52 | 129 | 257 | 0.1 |

Preparation of Final Blends

Five final blends (batches G01 to G05) with the different API batches were prepared. The formulations of the cores (25 mg and 100 mg dose strength, calculated as free base form) are shown in Table 2.

TABLE 2

Formulation 25 mg and 100 mg dose strength (calculated as free base form; i.e. the free base equivalent thereof)

| Component | mg per 25 mg tablet | mg per 100 mg tablet |
|---|---|---|
| N-[5-(aminosulfonyl)-4-methyl-1,3-thiazol-2-yl]-N-methyl-2-[4-(2-pyridinyl)-phenyl]acetamide mono methanesulfonic acid monohydrate | 32.3 (salt) | 129.0 (salt) |
| Microcrystalline cellulose | 60.9 | 243.4 |
| Croscarmellose sodium | 9.8 | 39.0 |
| Mannitol | 20.0 | 80.1 |
| Silica, colloidal anhydrous | 1.3 | 5.0 |
| Magnesium stearate | 0.9 | 3.5 |
| Sum final blend | 125.2 | 500.0 |

The final blends were prepared by sieving the raw materials using a 1.0 mm sieve. N-[5-(aminosulfonyl)-4-methyl-1,3-thiazol-2-yl]-N-methyl-2-[4-(2-pyridinyl)-phenyl]acet-amide mono methanesulfonic acid monohydrate, i.e. the API, wherein the particle size distribution is in a range from 1 to 400 μm, microcrystalline cellulose, croscarmellose sodium, mannitol and silica colloidal anhydrous were mixed for 30 minutes in a free fall blender. Magnesium stearate was added, and the blends were mixed for additional 5 minutes. No problems were observed during the process.

The bulk properties of batches GO1 to G05 are shown in Tables 3 and 4.

TABLE 3

Bulk properties of final blends

| Parameter | G01 | G02 | G03 | G04 | G05 |
|---|---|---|---|---|---|
| Bulk density [g/ml] | 0.413 | 0.435 | 0.385 | 0.403 | 0.440 |
| Tapped density [g/ml] | 0.510 | 0.526 | 0.563 | 0.500 | 0.550 |
| Flowability [cot] | 1.25 | 1.16 | 0.893 | 1.09 | 1.28 |

A significant difference in bulk density was seen for batch G03. This was the final blend, which contains the micronised API. Therefore, the bulk density was lower compared to the blends, which contain coarser API.

Batch G03 also had the worst flowability of all final blends. This may also be explained by the use of micronised API.

Tabletting

Final blends from batches GO1 to G04 and a part of final blend batch G05 were compressed as a 100 mg dose strength as free base equivalent. The other part of the final blend batch G05 was compressed as a 25 mg dose strength as free base equivalent.

During compression of the 100 mg dose strength as free base equivalent batches GO1, G02, G04 and G05, no further problems occurred. Surprisingly, it was found that the tablet weight was fluctuating during compression of batch G03. Unexpectedly, problems with uniformity of weight occurred. In addition, the tablet mass was sticking to the tools. It was obvious that both problems were caused by use of the micronised API. Therefore, it is advantageous to omit a micronisation step for tabletting, which will result in better handling and less production time.

Compression of the 25 mg dose strength as free base equivalent batch G05 was done without problems.

The IPC (in process checks) data of batches GO1-G05 are shown in Tables 4 and 5.

TABLE 4

IPC data 100 mg strength as free base equivalent

| Parameter | Nominal value | G01 | G02 | G03 | G04 | G05 |
|---|---|---|---|---|---|---|
| Weight [mg] | 485-515 | 498 | 500 | 497 | 506 | 516 |
| Diameter [mm] | 10.8-11.2 | 12.1 | 12.1 | 12.1 | 12.1 | 12.1 |
| Height [mm] | determine | 5.7-5.8 | 5.7 | 5.7-5.8 | 5.7 | 5.6-5.7 |
| Hardness [N] | >50 | 73 | 70 | 67 | 74 | 87 |
| Disintegration [min] | <5 | 20-30 sec | 15-25 sec | 20-30 sec | 20-25 sec | 15-25 sec |

TABLE 5

| IPC data 25 mg strength as free base equivalent | | |
|---|---|---|
| Parameter | Nominal value | G05 |
| Weight [mg] | 122-128 | 127 |
| Diameter [mm] | 6.8-7.2 | 7.1 |
| Height [mm] | determine | 3.6-3.7 |
| Hardness [N] | >50 | 56 |
| Disintegration [min] | <5 | 20-28 sec |

Analytics

Tablets or capsules taken orally remain one of the most effective means of treatment available. The effectiveness of such dosage forms relies on the drug dissolving in the fluids of the gastrointestinal tract prior to absorption into the systemic circulation. The rate of dissolution of the tablet or capsule is therefore crucial.

Dissolution: The criteria for dissolution in media with a pH of 1 is Q=75 after 45 minutes.

Influence of particle size distribution on the dissolution: Dissolution of cores from batches GO1 to G05 was performed. The dissolution results are shown in FIG. 8 and Table 6.

TABLE 6

| Dissolution results for batches G01-G05 | | | | | | | | | |
|---|---|---|---|---|---|---|---|---|---|
| | 15 | | | 30 | | | 45 | | |
| Batch (as free base equivalent) | Average [%] | Min [%] | Max [%] | Average [%] | Min [%] | Max [%] | Average [%] | Min [%] | Max [%] |
| G01 100 mg | 90 | 83 | 97 | 93 | 85 | 99 | 96 | 90 | 99 |
| G02 100 mg | 82 | 80 | 84 | 90 | 88 | 91 | 91 | 90 | 94 |
| G03 100 mg | 100 | 98 | 101 | 100 | 97 | 102 | 100 | 98 | 102 |
| G04 100 mg | 99 | 97 | 100 | 100 | 98 | 102 | 101 | 101 | 102 |
| G05 100 mg | 90 | 87 | 93 | 99 | 98 | 102 | 103 | 102 | 105 |
| G05 25 mg | 102 | 101 | 104 | 104 | 102 | 105 | 104 | 102 | 105 |

The dissolution results of batches GO1-G05 are according to the specification. There is no significant difference in the dissolution of cores, which contains finer or coarser API.

Content Uniformity (CU): Content uniformity of batches GO1 to G04 was tested. The results are shown in Table 7.

TABLE 7

| CU results of batches G01-G04 | | | |
|---|---|---|---|
| Batch | Assay mean (%) | Standard deviation | Acceptance value |
| G01 | 98.2 | 1.1917 | 3.2 |
| G02 | 101.2 | 1.2599 | 3.0 |
| G03 | 97.9 | 3.1110 | 8.1 |
| G04 | 103.3 | 1.3640 | 5.1 |

All results comply with Ph.Eur. 2.9.40. Content uniformity of batch G03 is inferior compared to the content uniformity of the other batches. It is obvious that this is related to the problems during compression based on the micronized API.

CONCLUSIONS

The particle size distribution of the API has an influence on the bulk properties of the final blend and on the tabletting characteristics. Batch G03, which contains the micronized API, has a worse flowability. Therefore, problems with a uniform weight occurred during compression. In addition, sticking problems were observed, and the CU results of the cores are not as good as the results of the cores with non-micronized API. By use of non-micronized API there was no influence of the particle size distribution, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, on uniformity of weight and CU obtained. The results do not show a marked influence of the particle size distribution on the dissolution of the cores as they are all within the predefined ranges.

Example 3

Tablet comprising 60 mg of N-[5-(aminosulfonyl)-4-methyl-1,3-thiazol-2-yl]-N-methyl-2-[4-(2-pyridinyl)-phenyl]acetamide as free base equivalent (corresponding to 76.9 mg of crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to the invention), wherein at least 65 v/v % are N-[5-(aminosulfonyl)-4-methyl-1,3-thiazol-2-yl]-N-methyl-2-[4-(2-pyridinyl)-phenyl]acetamide mono methanesulfonic acid monohydrate particles, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$; content of active compound about 59% (based on an unvarnished tablet):

| | |
|---|---|
| crystalline N-[5-(aminosulfonyl)-4-methyl-1,3-thiazol-2-yl]-N-methyl-2-[4-(2-pyridinyl)-phenyl]acetamide mono methanesulfonic acid monohydrate | 76.9 mg |
| Avicel PH 101 | 118.0 mg |
| lactose, fine | 40.0 mg |
| Ac-Di-Sol | 20.0 mg |
| polyinylpyrrolidone 25 | 10.0 mg |
| magnesium stearate | 2.0 mg |
| total weight | 266.9 mg |

Example 4

Tablet comprising 50 mg of N-[5-(aminosulfonyl)-4-methyl-1,3-thiazol-2-yl]-N-methyl-2-[4-(2-pyridinyl)-phenyl]acetamide as free base equivalent (corresponding to 64 mg of crystalline N-[5-(aminosulfonyl)-4-methyl-1,3-thiazol-2-yl]-N-methyl-2-[4-(2-pyridinyl)-phenyl]acetamide mono methanesulfonic acid monohydrate), wherein at least 65 v/v % are N-[5-(aminosulfonyl)-4-methyl-1,3-thiazol-2-yl]-N-methyl-2-[4-(2-pyridinyl)-phenyl]acetamide mono methanesulfonic acid monohydrate particles, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$; content of active compound about 59% (based on an unvarnished tablet):

| | |
|---|---|
| crystalline N-[5-(aminosulfonyl)-4-methyl-1,3-thiazol-2-yl]-N-methyl-2-[4-(2-pyridinyl)-phenyl]acetamide mono methanesulfonic acid monohydrate | 64.0 mg |
| polyinylpyrrolidone 25 | 3.5 mg |
| microcrystalline cellulose | 20.0 mg |
| croscamellose sodium | 10.0 mg |
| magnesium stearate | 0.9 mg |
| optionally HPMC varnish | 3.0 mg |
| total weight | 101.4 mg |

Example 5

Crystal structure of N-[5-(aminosulfonyl)-4-methyl-1,3-thiazol-2-yl]-N-methyl-2-[4-(2-pyridinyl)phenyl]acetamide mono methanesulfonic acid monohydrate Formula $C_{19}H_{24}N_4O_7S_3$, M=516.62, F(000)=540, colorless plate, size 0.02·0.13·0.15 $mm^3$, triclinic, space group P−1, Z=2, a=9.4908(7)Å, b=9.5545(7) Å, c=14.4137(9) Å, a=86.130(3)°, β=72.104(3)°, γ=68.253(4)°, V=1153.68(15) $Å^3$, $D_{calc}$=1.487 $Mg.m^{-3}$. The crystal was measured on a Nonius KappaCCD diffractometer at 293 K using graphite-monochromated Mo $K_\alpha$-radiation with λ=0.71073 Å, $\Theta_{max}$=30.065°. Minimal/maximal transmission 0.95/0.99, μ=0.370 $mm^{-1}$. The COLLECT suite has been used for data collection and integration. Of 43492 reflections in total, 6761 were independent (merging r=0.026). From these, 4955 were considered observed (I>3.0σ(I)) and were used to refine 298 parameters. The structure was solved by direct methods using the program SIR92. Least-squares refinement against F was carried out on all non-hydrogen atoms using the program CRYSTALS. R=0.0313 (observed data), wR=0.0432 (all data), GOF=1.0736. Minimal/maximal residual electron density=−0.28/0.33 e $Å^{-3}$. Chebychev polynomial weights were used to complete the refinement.

Table 8 shows single-crystal structure parameters for N-[5-(aminosulfonyl)-4-methyl-1,3-thiazol-2-yl]-N-methyl-2-[4-(2-pyridinyl)phenyl]acetamide mono methanesulfonic acid monohydrate.

TABLE 8

Single-crystal structure parameters for N-[5-(aminosulfonyl)-4-methyl-1,3-thiazol-2-yl]-N-methyl-2-[4-(2-pyridinyl)phenyl]acetamide mono methanesulfonic acid monohydrate

| Parameter | Value |
|---|---|
| formula | $C_{19}H_{24}N_4O_7S_3$ |
| formula weight | 516.62 g/mol |
| Z, calculated density | 2, 1.487 Mg × $m^{-3}$ |
| F(000) | 540 |
| description and size of crystal | Colorless plate, 0.02 × 0.13 × 0.15 $mm^3$ |
| absorption coefficient | 0.370 $mm^{-1}$ |
| min/max transmission | 0.95/0.99 |
| temperature | 293K |
| radiation (wavelength) | Mo K□□(□ = 0.7103 Å) |
| crystal system, space group | Triclinic, P −1 |
| a | 9.4908 (7) Å |
| b | 9.5545(7) Å |
| c | 14.4137(9) Å |
| □ | 86.130(3)° |
| □ | 72.104(3)° |
| Y | 68.253(4)° |
| V | 1153.68(15) $Å^3$ |
| min/max Θ | 2.426°/30.065° |
| number of collected reflections | 43492 |
| number of independent reflections | 6761 (merging r = 0.026) |
| number of observed reflections | 4955 (I > 3.0□(1)) |
| number of refined parameters | 298 |
| r | 0.0313 (observed data with) |
| rW | 0.0432 (all data) |
| goodness of fit | 1.0736 |
| residual electron density | −0.28/0.33 e$Å^{-3}$ |

Example 6

Single-Dose Escalation and Pharmacokinetics

An advantage of the tablets according to the invention is that the tablet will have an optimised dissolution rate based on the particle size distribution of the crystalline form of N-[5-(aminosulfonyl)-4-methyl-1,3-thiazol-2-yl]-N-methyl-2-[4-(2-pyridinyl)-phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, and thus, the drug may be absorbed into the blood stream much faster compared to N-[5-(aminosulfonyl)-4-methyl-1,3-thiazol-2-yl]-N-methyl-2-[4-(2-pyridinyl)-phenyl]acetamide as crystalline free base form. Furthermore, the surprising dispersion times obtained with tablets according to the invention are advantageous for swallowable tablets. In a further embodiment, the tablets according to the invention can be presented for dispersion in water.

Therefore, pharmacokinetic studies in human subjects were undertaken following both single and multiple dose administrations of the crystalline mono mesylate monohydrate salt of N-[5-(aminosulfonyl)-4-methyl-1,3-thiazol-2-yl]-N-methyl-2-[4-(2-pyridinyl)phenyl]-acetamide, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$.

Single oral doses of the crystalline mono mesylate monohydrate salt of N-[5-(aminosulfonyl)4methyl1,3thiazol-2-yl]-N-methyl-2-[4-(2-pyridinyl)phenyl]acetamide using the formulations according to example 2, Table 2, were administered to six volunteers per dose step. The overall shape of the plasma concentrations vs. time profiles were similar across all doses (see FIG. 9 and FIG. 12).

There was a rapid and continuous increase of plasma concentrations of the free base of N-[5-(aminosulfonyl) 4methyl1,3thiazol-2-yl]-N-methyl-2-[4-(2-pyridinyl)phenyl]acetamide switching into a period of markedly slower absorption rate and evidence of a plateau effect in exposure. Thereafter, for all doses investigated, there was a decrease of concentrations of the free base of N-[5-(aminosulfonyl) 4methyl1,3thiazol-2-yl]-N-methyl-2-[4-(2-pyridinyl)phenyl]acetamide starting after 4.0 to 4.5 hours post administration of the crystalline mono mesylate monohydrate salt of N-[5-(aminosulfonyl)4methyl1,3thiazol-2-yl]-N-methyl-2-[4-(2-pyridinyl) phenyl]acetamide. This phase was followed by a phase of prolonged exposure, which was characterised by a long half-life, which is favorable for the treatment of infectious diseases. The mean terminal elimination half-life ($t_{1/2z}$) ranged between 52 h and 85 h. For doses from 5 mg to 480 mg as free base equivalent there was a dose-proportional increase in $AUC_{0-\infty}$ (AUC, area under curve); a single dose of 600 mg as free base equivalent did not cause any further rise of exposure as shown by $AUC_{0-\infty}$ (see FIG. 9 and FIG. 12).

Maximum plasma concentrations were linearly related to doses from 5 mg to 400 mg as free base equivalent. At the higher dose up to 600 mg as free base equivalent no further increase of exposure was obtained as shown by the both $C_{max}$ and $AUC_{0-\infty}$. Median $t_{max}$ ranged from 1.5 to 4.25 hours without any obvious relation to dose. A summary of single-dose pharmacokinetic parameters is shown in Table 9.

Table 9: Pharmacokinetic parameters after ascending single oral doses of crystalline mono mesylate monohydrate salt of N-[5-(aminosulfonyl)-4-methyl-1,3-thiazol-2-yl]-N-methyl-2-[4-(2-pyridinyl)phenyl]acetamide in the formulations according to the formulation described on page 20 wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$.

In the following the abbreviations used in Table 9 are defined. $AUC_{0-\infty}$: Area under the analyte vs. time concentration from time of administration up to infinity, calculated $$AUC_{0-\infty} = AUC_{0-last} + \frac{C_{last}}{\lambda_z}$$

wherein $AUC_{0-last}$ is defined as the area under the analyte vs. time concentration up to time of the last qualifiable concentration, calculated by linear up/log down summation and $C_{last}$ is defined as last quantifiable observed analyte concentration. $\lambda_z$ is the apparent terminal elimination rate constant, determined by linear regression of terminal points of Inlinear analyte concentration-time curve. $C_{max}$ is the maximal observed analyte concentration and $t_{max}$ is the time to reach $C_{max}$, $t_{1/2z}$ is defined as the apparent terminal elimination half-life, calculated as $$t_{1/2z} = \frac{\ln(2)}{\lambda_z},$$

wherein $\lambda_z$ is defined as above.

MRT: Mean Residence Time; calculated AUMC divided by AUC, wherein AUMC is the area under the first moment of the concentration-time curve from zero up to ∞ with extrapolation of the terminal phase and AUC is the area under the concentration-time curve from zero up to ∞ with extrapolation of the terminal phase. CL/F refers to the clearance after oral administration of a drug and $A_e$ refers to the amount of drug excreted in the urine.

TABLE 9

| dose [mg] | parameter (means; n = 6 volunteers/dose) | | | | | | |
|---|---|---|---|---|---|---|---|
| free base equivalent | $AUC_{0-\infty}$ [ng · h/mL] | $C_{max}$ [ng/mL] | $t_{max}$[a] [h] | $t_{1/2z}$ [h] | MRT [h] | CL/F [L/h] | $A_e$ [% of dose] |
| 5 | 5800 | 74 | 4.00 | 80 | 117 | 0.89 | 0 |
| 10 | 11670 | 170 | 1.50 | 85 | 116 | 0.87 | 0 |
| 20 | 18540 | 234 | 2.77 | 76 | 105 | 1.10 | 0 |
| 40 | 40680 | 608 | 3.50 | 72 | 94 | 1.00 | 0 |
| 80, males | 87220 (99790)[b] | 1306 (1499)[b] | 2.50 | 74 | 94 | 0.94 | 0.16 |
| 80, females | 96230 (90050)[b] | 1999 (1853)[b] | 4.00 | 58 | 77 | 0.85 | 0.31 |
| 160 | 130800 | 2613 | 3.50 | 63 | 83 | 1.28 | 0.15 |
| 240 | 216900 | 3600 | 4.00 | 64 | 82 | 1.15 | 0.21 |
| 320 | 241100 | 4648 | 2.25 | 57 | 70 | 1.47 | 0.16 |
| 400 | 320300 | 6926 | 4.25 | 57 | 64 | 1.31 | 0.15 |
| 480 | 387200 | 6921 | 3.25 | 53 | 72 | 1.33 | 0.26 |
| 600 | 320800 | 6442 | 4.25 | 52 | 65 | 2.00 | 0.09 |

[a]for tmax the median is given,
[b]value normalized to body weight for a 70 kg subject;

Based on data for the 80 mg dose as free base equivalent (see also FIG. 13), women appeared to exhibit a higher exposure compared to males according to $AUC_{0-\infty}$ and $C_{max}$ (see Table 9). However, normalization to body weight revealed that this apparent difference could be explained by the lower body weight of the female volunteers compared to males (see FIG. 13).

Summary of the Results of Example 6

For doses from 5 mg to 400 and 480 mg as free base equivalent, respectively, there was a linear, i.e. dose-proportional, increase in $AUC_{0-\infty}$ and $C,_{max}$ with dose; higher doses do not further increase the exposure. The mean terminal elimination half-life ($t_{1/2z}$) ranged between 52 h and 85 h (see FIG. 12). No clinical relevant gender-related difference in exposure was detected for a single dose of 80 mg as free base equivalent (see FIG. 13).

Example 7

Multiple-Dose Escalation and Pharmacokinetics

For the three doses of the mono mesylate monohydrate salt of N-[5-(aminosulfonyl)-4-methyl-1,3-thiazol-2-yl]-N-methyl-2-[4-(2-pyridinyl)phenyl]acetamide in formulation according to example 1, Table 2, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, investigated (5, 25, and 100 mg as free base equivalent; once per day oral administration, 20 days), the individual concentration-time curves of the free base N-[5-(aminosulfonyl)-4-methyl-1,3-thiazol-2-yl]Nmethyl-2-[4-(2-pyridinyl) phenyl]acetamide at day 1 (after the first administration) were very similar in their general shape and slope to those profiles obtained in the single dose escalation trial (see Example 6). As for the single dose escalation trial presented in Example 6, there were dose-proportional increases in $AUC_{0-24h}$ and $C_{max}$ at day 1.

During the 20-day treatment with administrations of the mono mesylate monohydrate salt of N-[5-(aminosulfonyl)-4-methyl-1,3-thiazol-2-yl]-N-methyl-2-[4-(2-pyridinyl)phenyl]-acetamide, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, once daily, the attainment of steady-state conditions was demonstrated by virtually identical minimal or "trough" concentrations of the free base of N-[5-(aminosulfonyl)-4-methyl-1,3-thiazol-2-yl]-N-methyl-2-[4-(2-pyridinyl)phenyl]acetamide achieved between days 9 and 13. At steady state, there was a low inter-individual variability of minimal or "trough" concentrations with CVs (coefficient of variations) between 16.7 and 21.7% (day 21). For all doses, the individual and mean concentration-time curves of the free base of N-[5-(aminosulfonyl)-4-methyl-1,3-thiazol-2-yl]-N-methyl-2-[4-(2-pyridinyl)phenyl]acet-amide at day 21 were very similar in their shape and slope to those profiles obtained at day 1.

Table 10 summarizes the steady-state pharmacokinetics of the free base of N-[5-(aminosulfonyl)-4-methyl-1,3-thiazol-2-yl]-N-methyl-2-[4-(2-pyridinyl)phenyl]acetamide.

Table 10: Steady state pharmacokinetic parameters of the free base N-[5-(aminosulfonyl)-4-methyl-1,3-thiazol-2-yl] N-methyl-2-[4-(2-pyridinyl)phenyl]acetamide at day 21 after daily administrations of 5, 25, or 100 mg as free base equivalent of the mono mesylate monohydrate salt of N-[5-(aminosulfonyl)-4-methyl-1,3-thiazol-2-yl]-N-methyl-2-[4-(2-pyridinyl)phenyl]acetamide in formulation according to example 2, Table 2, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, to healthy volunteers (n=12 per dose).

In the following the abbreviations used in Table 10 are defined. $C_{trough}$: measured plasma concentration immediately before dosing at day 21 (at the end of the dosing interval at steady state); $AUC_t$, i.e. the steady state AUC (area under the curve) within the dosing interval of 24 hours, $C_{max,ss}$ refers to the maximal observed analyte concentration at steady state. $C_{av}$ is defined as average plasma concentration during the dosing interval the mono mesylate monohydrate salt of N-[5-(aminosulfonyl)-4-methyl-1,3-thiazol-2-yl]-N-methyl-2-[4-(2-pyridinyl)phenyl]acetamide at steady state, R-AUC refers to the accumulation ratio of the AUC, i.e. $AUC_t/AUC_{0-24h,day1}$, R-$C_{max}$ refers to accumulation ratio of $C_{max}$, i.e. $C_{max,ss}/C_{max,day1}$; $t_{1/2z}$ is defined as above

TABLE 10

| dose [mg] as free base equivalent | $C_{trough}$ [ng/mL] | $AUC_T$ [ng · h/mL] | $C_{max,\ ss}$ [ng/mL] | $C_{av}$ [ng/mL] | R-AUC | R-$C_{max}$ | $t_{1/2z}$ [h] |
|---|---|---|---|---|---|---|---|
| 5 | 187 | 5094 | 301 | 213 | 5.2 | 5.0 | 82.6 |
| 25 | 832 | 23430 | 1358 | 977 | 5.3 | 5.3 | 68.6 |
| 100 | 3743 | 108800 | 6358 | 4540 | 5.1 | 5.3 | 59.8 |

For the three doses applied, there was a dose-proportional increase for all measures of exposure at steady state ($C_{trough}$, $AUC_t$, $C_{max,ss}$, and $C_{av}$) (see Table 10). For both AUC and $C_{max}$, the accumulation ratio R of all doses applied was very similar being approximately a factor of 5 (see Table 10). The time to reach $C_{max,ss}$ was similar for the three doses (0.5-4.5 h). The peak-trough fluctuation at steady-state ranged between 59 and 64%. Elimination half-life was in the same range as after single-dose application with 82.6 h (5 mg), 68.6 h (25 mg), and 59.8 h (100 mg). The apparent total clearance (CL/F) was estimated to be similar for all doses investigated (0.99-1.08 L/h).

Summary of the Results of Example 7

Under steady-state conditions, an increase in the dose of mono mesylate monohydrate salt of N-[5-(aminosulfonyl)-4-methyl-1,3-thiazol-2-yl]-N-methyl-2-[4-(2-pyridinyl)phenyl]acetamide in formulation according to example 2, Table 2, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, resulted in a proportional increase in exposure to the resultant free base of N-[5-(aminosulfonyl)-4-methyl-1,3-thiazol-2-yl]-N-methyl-2-[4-(2-pyridinyl)phenyl]acetamide. In general, plasma concentrations at steady state are to be expected to be approximately five times higher than after single dose administration of the same dose. This should be a reflection of the half-life and dosing interval. Inter-individual variability of steady state exposure was quite low as revealed by a low coefficient of variation, e.g. for minimal or "trough" concentrations and peak-trough fluctuations. Rate of elimination and terminal half-lives at steady-state were comparable to the single dose situation Example 8

Pharmacokinetic/Pharmacodynamic Correlation

To assess the pharmacokinetic/pharmacodynamic profile the effective dose of the free base of N-[5-(aminosulfonyl)-4-methyl-1,3-thiazol-2-yl]-N-methyl-2-[4-(2-pyridinyl)phenyl]-acetamide was validated in a murine HSV skin infection model and associated plasma concentrations were determined (data not shown).

The results were compared with the effective concentration of the free base of N-[5-(aminosulfonyl)-4-methyl-1,3-thiazol-2-yl]-N-methyl-2-[4-(2-pyridinyl)phenyl]acetamide in cell culture and correlated to exposures reached in healthy male volunteers in single and multiple dose phase I trials (see FIGS. 9-13).

Oral doses of 5 mg/kg of the free base of N-[5-(aminosulfonyl)-4-methyl-1,3-thiazol-2-yl]-N-methyl-2-[4-(2-pyridinyl)phenyl]acetamide or higher once daily doses for four days completely suppressed the murine infection (data not shown). Associated plasma concentrations in mice determined with a single oral dose of 10 mg/kg of the free base form were well above the cell culture $EC_{90}$ adjusted for protein binding over the entire dosing interval of 24 h. In healthy male volunteers these plasma concentrations were covered by a single dose of 40 mg as free base equivalent to the crystalline mono mesylate monohydrate salt of N-[5-(aminosulfonyl)-4-methyl-1,3-thiazol-2-yl]-N-methyl-2-[4-(2-pyridinyl)phenyl]acetamide (see FIG. 10) and at steady state by daily doses of 25 mg as free base equivalent (see FIG. 11) for 21 days. In both settings the resultant free base of N-[5-(aminosulfonyl)-4-methyl-1,3-thiazol-2-yl]-N-methyl-2-[4-(2-pyridinyl)phenyl]-acetamide was safe and well tolerated up to the highest dose tested.

In summary, the free base of N-[5-(aminosulfonyl)-4-methyl-1,3-thiazol-2-yl]-N-methyl-2-[4-(2-pyridinyl)phenyl]acetamide exhibits advantageous PK/PD profiles in non-clinical studies and exposures required to suppress HSV replication were reached in humans.

Specifically, the free base of N-[5-(aminosulfonyl)-4-methyl-1,3-thiazol-2-yl]-N-methyl-2-[4-(2-pyridinyl)phenyl]acetamide, resultant from the herein described crystalline mono mesylate monohydrate salt of N-[5-(aminosulfonyl)-4-methyl-1,3-thiazol-2-yl]-N-methyl-2[4-(2-pyridinyl)phenyl]acetamide wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, exhibits advantageous PK/PD profiles in non-clinical studies and exposures required to suppress HSV replication were reached in humans.

These results clearly demonstrate that using the mono mesylate monohydrate salt of N-[5-(aminosulfonyl)-4-methyl-1,3-thiazol-2-yl]-N-methyl-2-[4-(2-pyridinyl)phenyl]acetamide, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ in the formulations as described above, a once daily dose (or even a less frequent administration) is sufficient for reaching an appropriate plasma concentration for the treatment of viral diseases, e.g. infection by a herpes virus or herpes viruses. In a further human trial it has been shown that the administration of a higher dose of 400 mg to 600 mg as free base equivalent and preferably about 500 mg as free base equivalent of the crystalline mono mesylate monohydrate salt of the present invention is also sufficient for reaching an appropriate plasma concentration for the treatment of viral diseases, e.g. infection by a herpes virus or herpes viruses.

N-[5-(aminosulfonyl)-4-methyl-1,3-thiazol-2-yl]-N-methyl-2-[4-(2-pyridinyl)phenyl]acetamide mono mesylate monohydrate (200441092)

free base of N-[5-(aminosulfonyl)-4-methyl-1,3-thiazol-2-yl]-N-methyl-2-[4-(2-pyridinyl)phenyl]acetamide (200472682), N-[5-(aminosulfonyl)-4-methyl-1,3-thiazol-2-yl]-N-methyl-2-[4-(2-pyridinyl)phenyl]acetamide, granulation of free base using 1 equivalent of methanesulfonic acid according to WO 2006/103011, example 5 (200472053);

lowest curve shows blank granulation matrix (200472054). A 1:1 (weight per weight) mixture of the free base and the mono mesylate monohydrate was analyzed with X-ray powder diffraction as calibration of the ratio of free base to salt. The ratio was calculated based on integration and shows the granulation mixture having a content of the mono mesylate monohydrate form of 8 to 12 percent.

Figure 1:
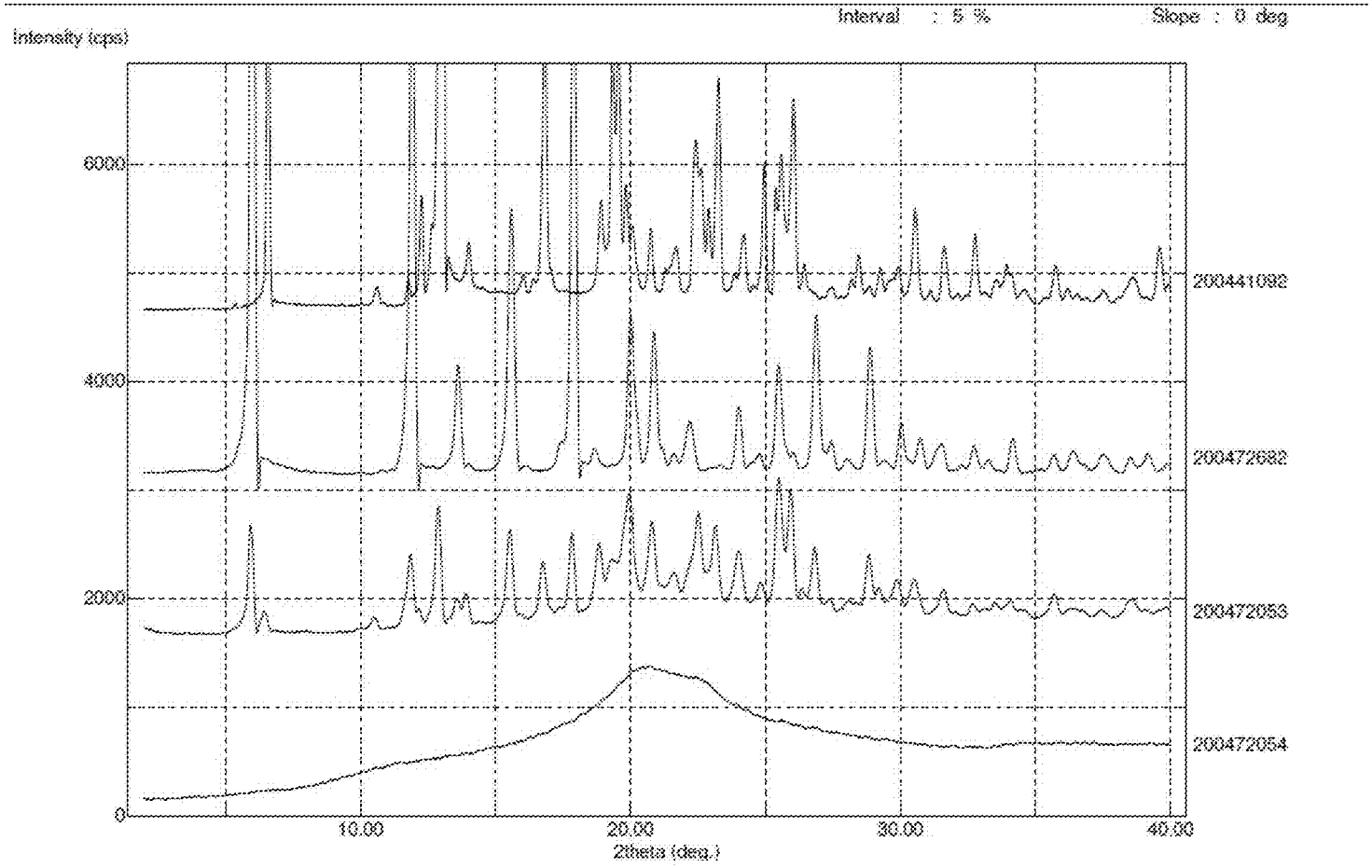
FIG. 1 Shows the overlay of X-ray powder diffractions obtained after granulation experiments; from top to bottom.
Figure 2:
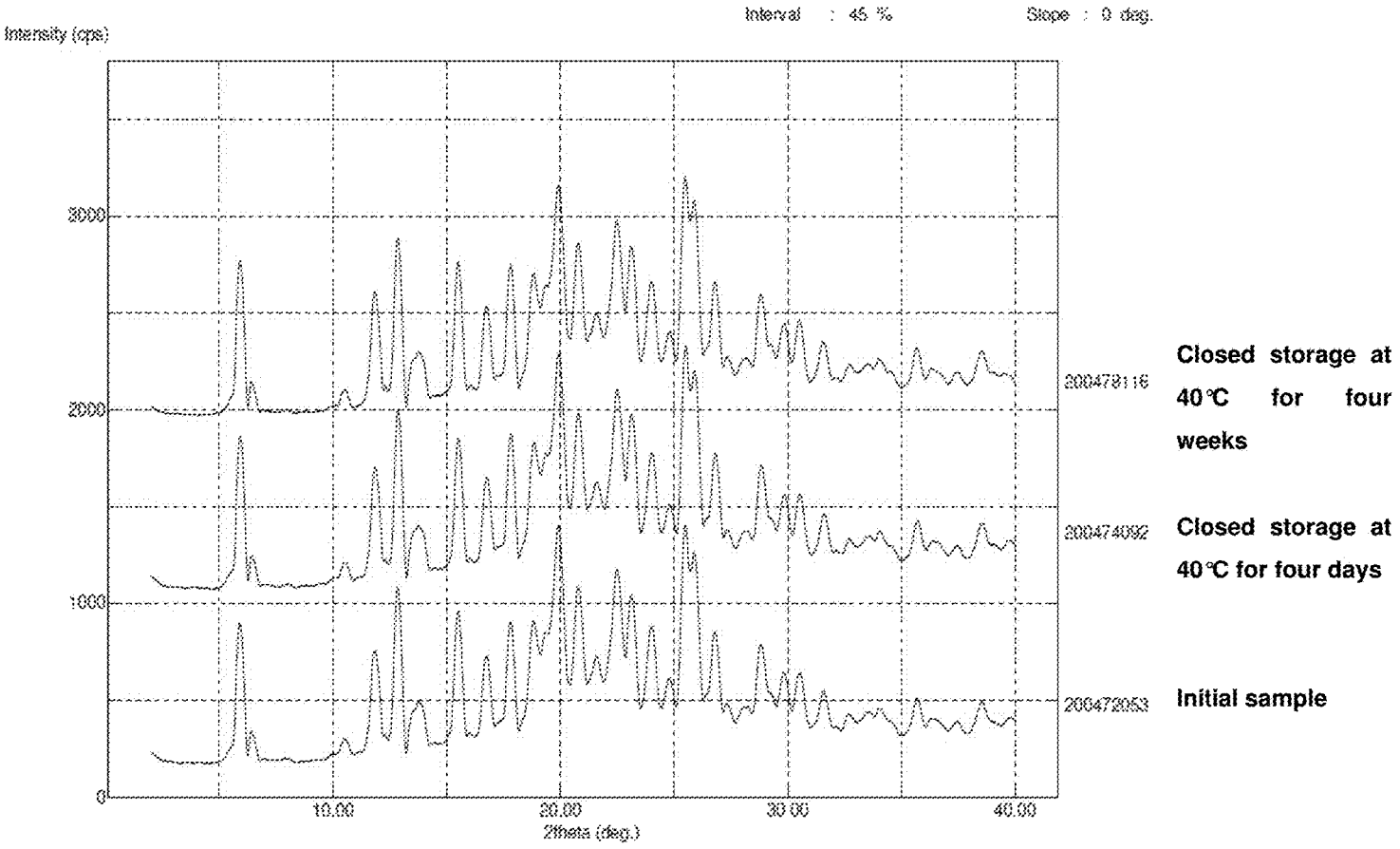

FIG. 2 Shows the overlay of X-ray powder diffraction spectra of granulations of a mixture of crystalline N-[5-(aminosulfonyl)-4-methyl-1,3-thiazol-2-yl]-N-methyl-2-[4-(2-pyridinyl)phenyl]acetamide mono methanesulfonic acid monohydrate with N-[5-(aminosulfonyl)-4-methyl-1,3-thiazol-2-yl]-N-methyl-2-[4-(2-pyridinyl)phenyl]acetamide mono methanesulfonic acid after closed storage at 40° C. for four weeks (top; 200478116), after closed storage at 40° C. for four days (middle; 200474092) and of the initial sample, i.e. the mixture of N-[5-(aminosulfonyl)-4-methyl-1,3-thiazol-2-yl]-N-methyl-2-[4-(2-pyridinyl)phenyl]acetamide mono methanesulfonic acid monohydrate with N-[5-(aminosulfonyl)-4-methyl-1,3-thiazol-2-yl]-N-methyl-2-[4-(2-pyridinyl)phenyl]acetamide mono methanesulfonic acid (200472053).

Figure 3A:
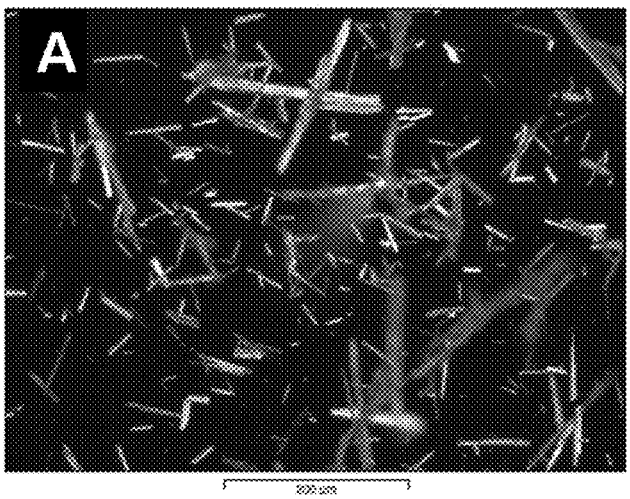
Figure 3B:
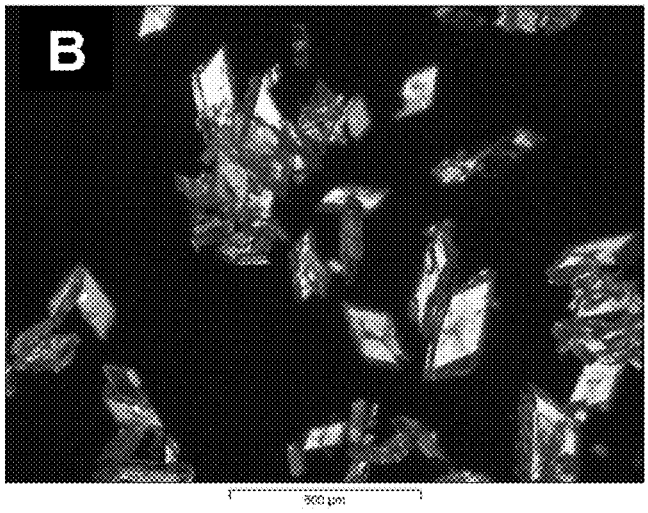

FIG. 3A Shows microscope pictures of the free base form of N-[5-(aminosulfonyl)-4-methyl-1,3-thiazol-2-yl]-N-methyl-2-[4-(2-pyridinyl)phenyl]

acetamide. FIG. 3B Shows microscope pictures of crystalline N-[5-(aminosulfonyl)-4-methyl-1,3-thiazol-2-yl]-N-methyl-2-[4-(2-pyridinyl)phenyl]acetamide mono methanesulfonic acid monohydrate.

Figure 3C:
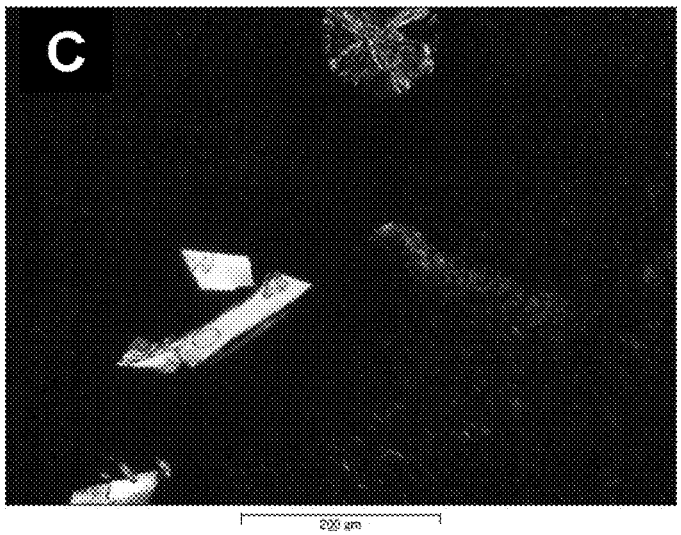

FIG. 3C Shows microscope pictures of spontaneous crystallized material after addition of methanesulfonic acid.

Figure 4:
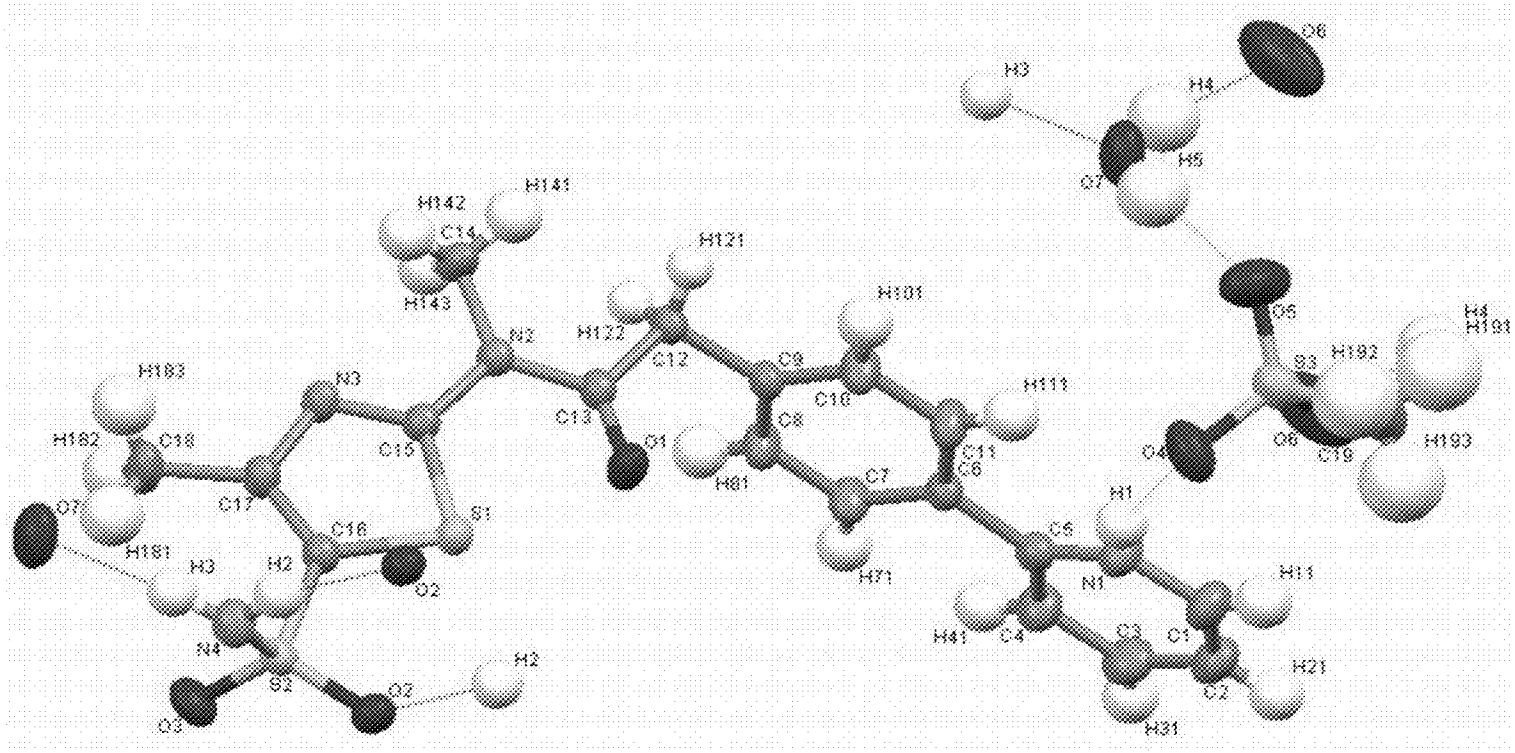

FIG. 4 Shows the X-ray structure of the crystalline N-[5-(aminosulfonyl)-4-methyl-1,3-thiazol-2-yl]-N-methyl-2-[4-(2-pyridinyl)phenyl]acetamide mono methanesulfonic acid monohydrate with indicated hydrogen bridges. It is shown that the nitrogen atom in the pyridinyl ring (right side bottom) is protonated and that a hydrogen bridge is formed between the hydrogen, which protonates the pyridinyl ring nitrogen and one oxygen of the mesylate anion, and another hydrogen bridge is formed between another oxygen of the mesylate anion and the hydrogen of the water molecule while the other hydrogen of the water molecule form a hydrogen bridge with the oxygen of another mesylate anion.

Figure 5:
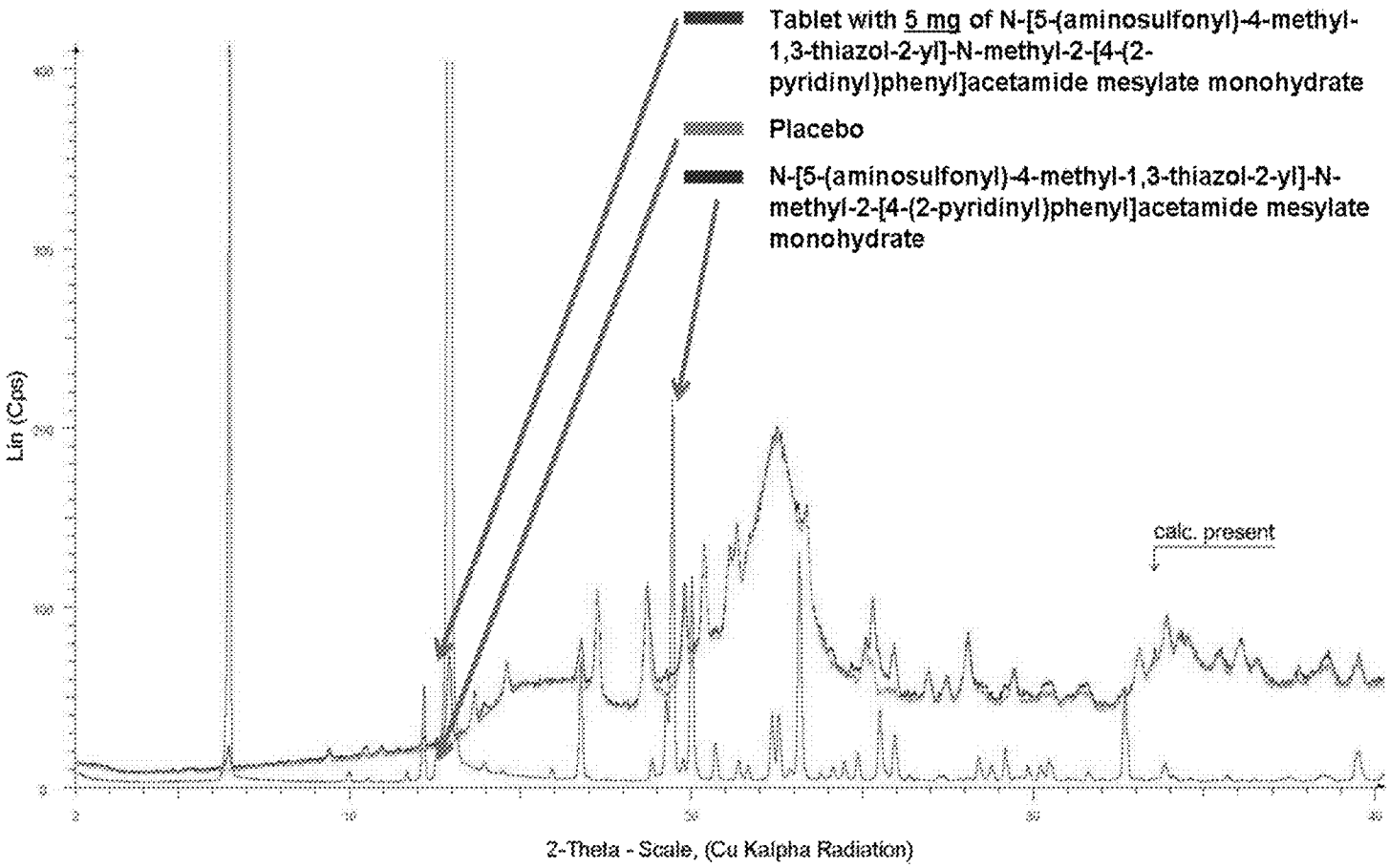

FIG. 5 Shows the X-ray powder diffraction spectra of a film-coated tablet with 5 mg as free base equivalent of crystalline N-[5-(aminosulfonyl)-4-methyl-1,3-thiazol-2-yl]-N-methyl-2-[4-(2-pyridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ (Nr. 1), a placebo tablet (Nr. 2) and of N-[5-(aminosulfonyl)-4-methyl-1,3-thiazol-2-yl]-N-methyl-2-[4-(2-pyridinyl)phenyl]acetamide mono methanesulfonic acid monohydrate (Nr. 3) after 24 months at 25° C.

Figure 6:
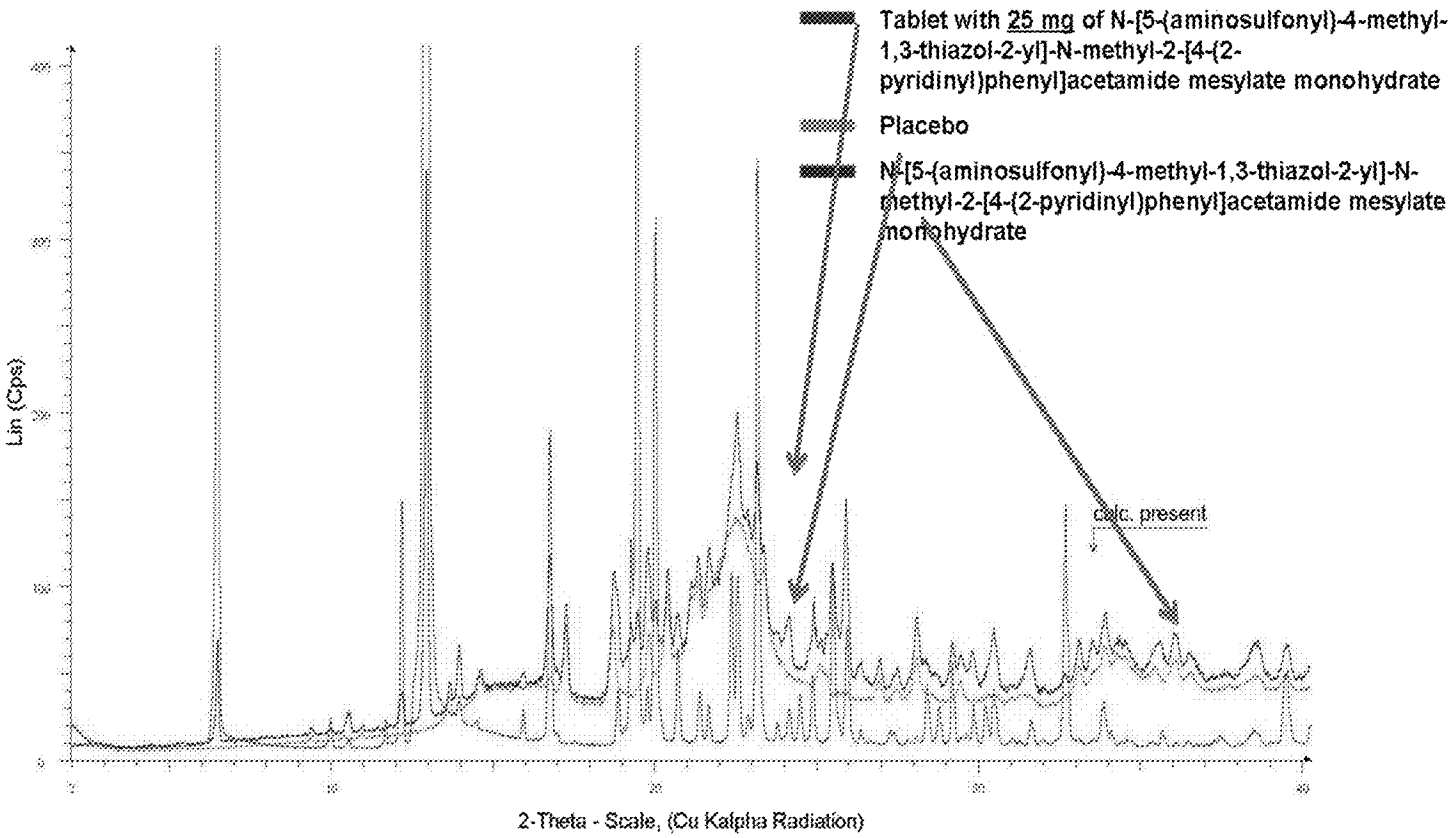

FIG. 6 Shows the X-ray powder diffraction spectra of a film-coated tablet with 25 mg as free base equivalent of crystalline N-[5-(aminosulfonyl)-4-methyl-1,3-thiazol-2-yl]-N-methyl-2-[4-(2-pyridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 m2/g, and more preferably defined by d(0.1) from 10 to 75 μm, d(0.5) from 100 to 175 μm, d(0.9) from 200 to 350 μm with a specific surface area of the particles less than 0.3 $m^2/g$ (Nr. 1), a placebo tablet (Nr. 2) and of N-[5-(aminosulfonyl)-4-methyl-1,3-thiazol-2-yl]-N-methyl-2-[4-(2-pyridinyl)phenyl]acetamide mono methanesulfonic acid monohydrate (Nr. 3) after 24 months at 25° C.

Figure 7:
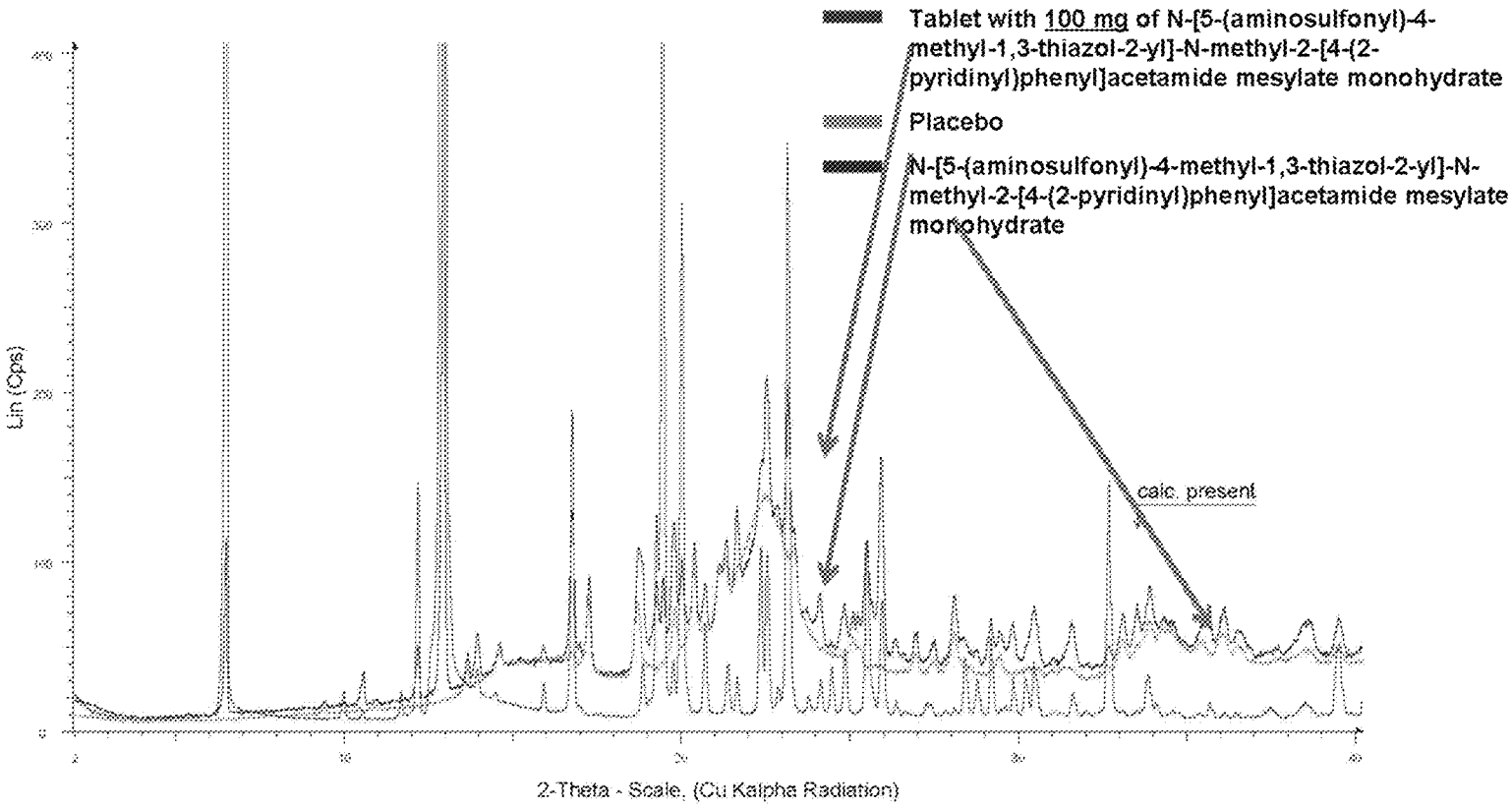

FIG. 7 Shows the X-ray powder diffraction spectra of a film-coated tablet with 100 mg as free base equivalent of crystalline N-[5-(aminosulfonyl)-4-methyl-1,3-thiazol-2-yl]-N-methyl-2-[4-(2-pyridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ (Nr. 1), a placebo tablet (Nr. 2) and of N-[5-(aminosulfonyl)-4-methyl-1,3-thiazol-2-yl]-N-methyl-2-[4-(2-pyridinyl)phenyl]acetamide mono methanesulfonic acid monohydrate (Nr. 3) after 24 months at 25° C.

Figure 8:
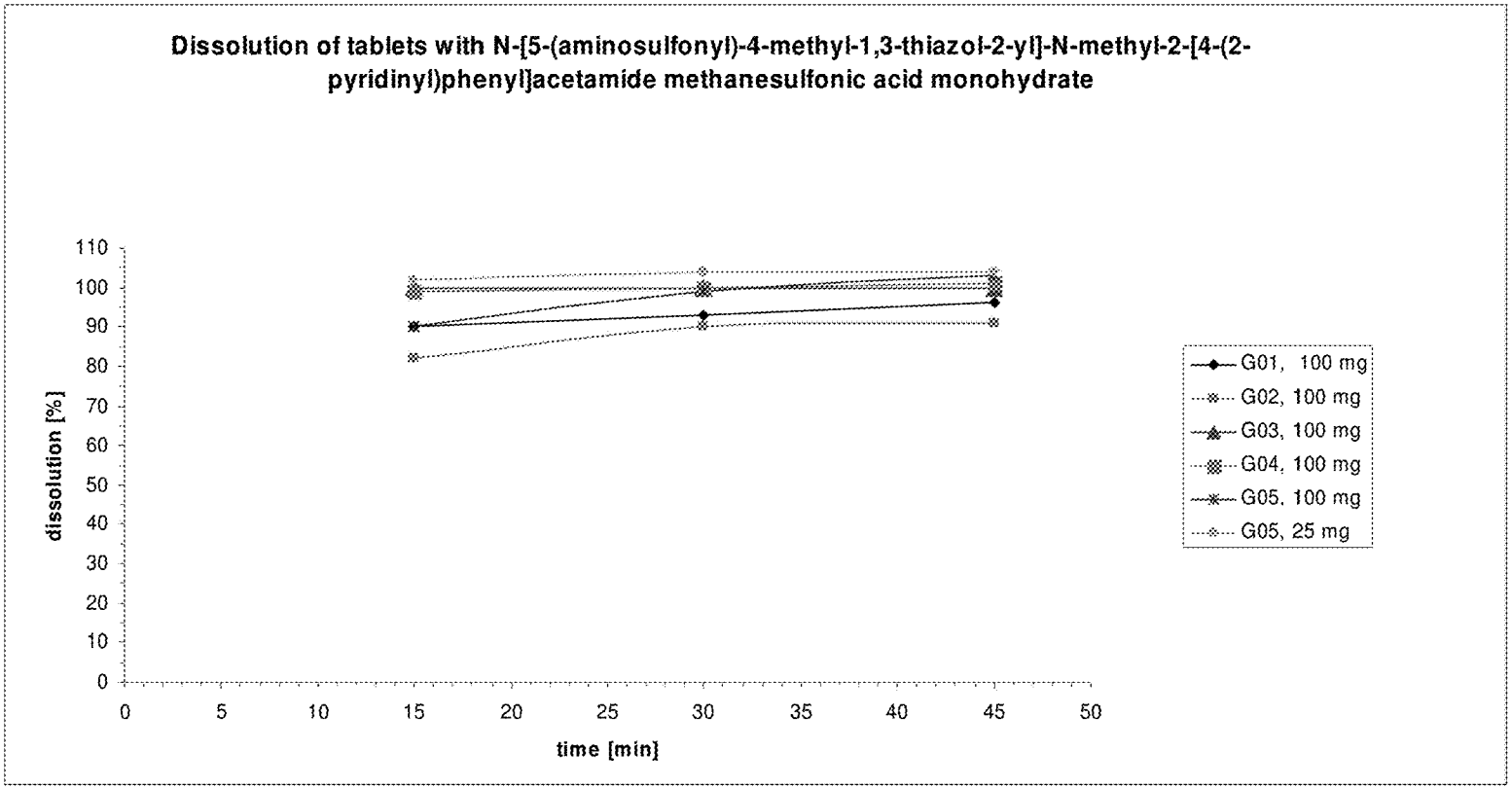

FIG. 8 Shows the dissolution curves of the six different tablets according to Table 7 (G01-G05 indicated by marked lines and arrows).

Figure 9:
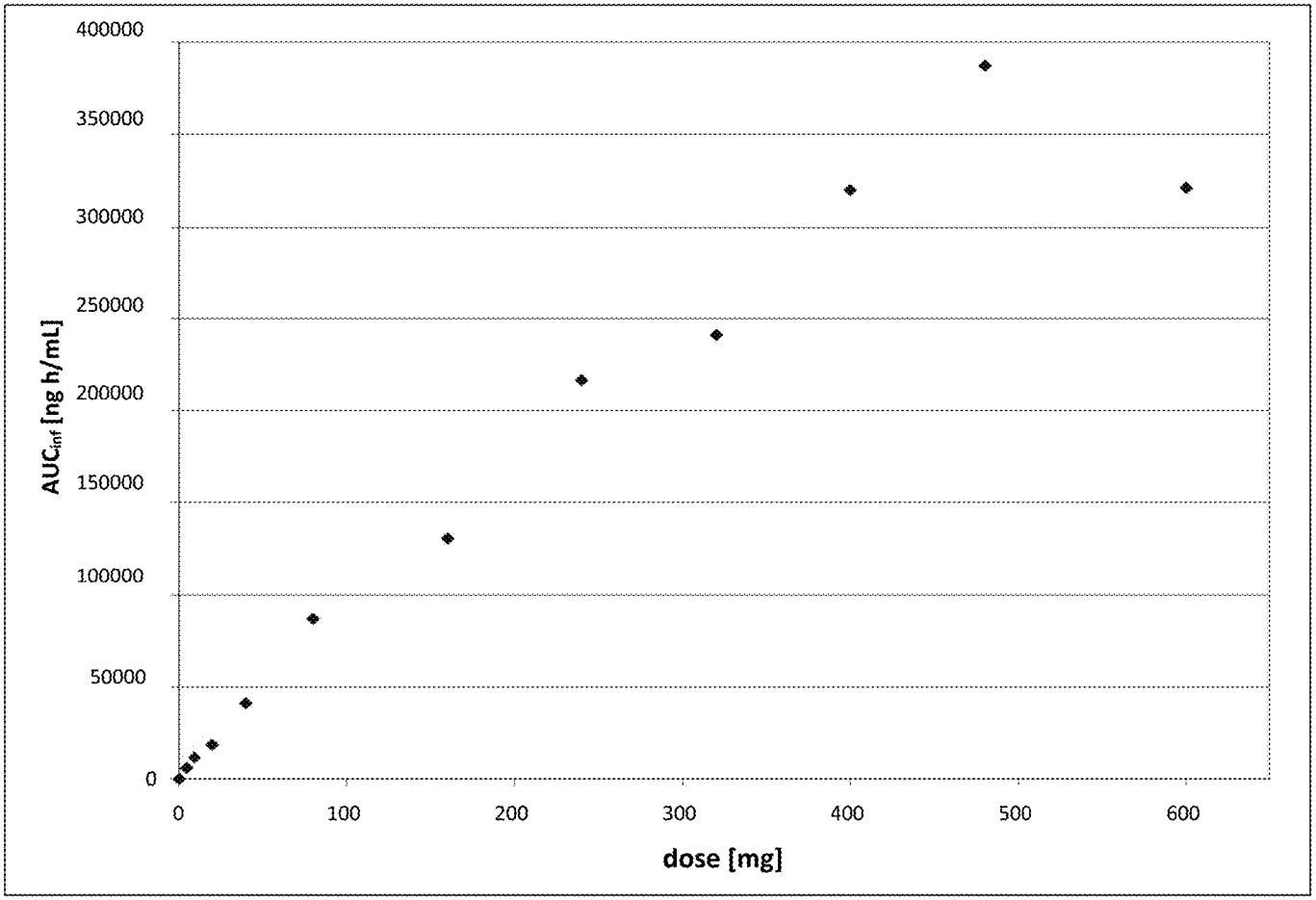

FIG. 9 Shows the relationship between single doses [mg] (5 mg-600 mg as free base equivalent) of tablets containing crystalline N-[5-(aminosulfonyl)-4-methyl-1,3-thiazol-2-yl]-N-methyl-2-[4-(2-pyridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$, and AUCinf [ng*h/mL] (identical to $AUC_{0-\infty}$), measured as the free base of N-[5-(aminosulfonyl)-4-methyl-1,3-thiazol-2-yl]-N-methyl-2-[4-(2-pyridinyl)phenyl]acetamide.

Figure 10:
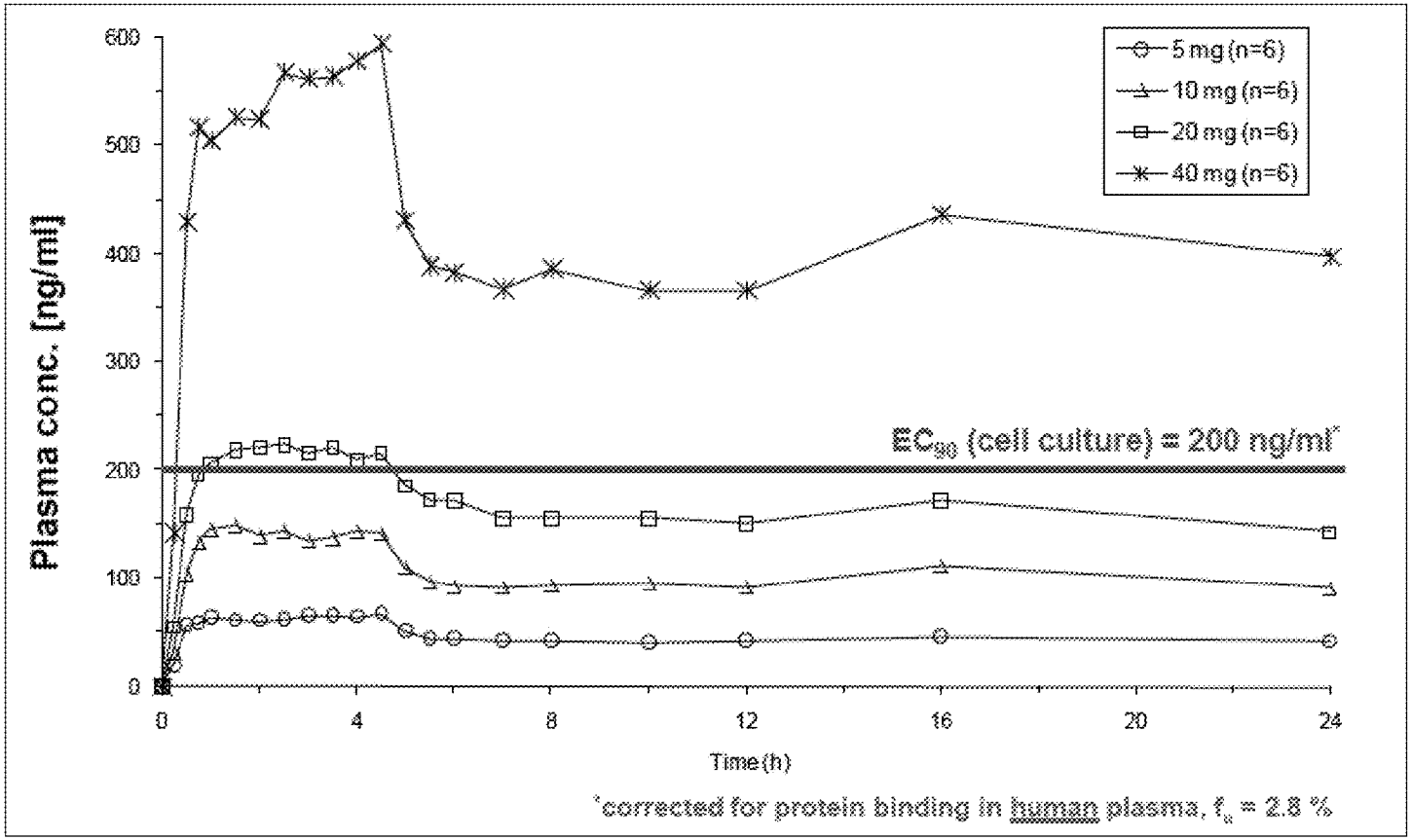

FIG. 10 Shows plasma time curves of the free base of N-[5-(aminosulfonyl)-4-methyl-1,3-thiazol-2-yl]-N-methyl-2-[4-(2-pyridinyl)phenyl]acetamide measured by HPLC in plasma of healthy male volunteers (n=6) after a single oral dose of tablets containing 5 mg; 10 mg; 20 mg and 40 mg as free base equivalent of crystalline N-[5-(aminosulfonyl)-4-methyl-1,3-thiazol-2-yl]-N-methyl-2-[4-(2-pyridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$. The four different doses were administered as immediate release tablets and blood was collected at indicated time points after administration. The free base concentration was measured by HPLC in plasma. The $EC_{90}$ derived from cell culture was corrected for protein binding taking into account the fraction unbound of N-[5-(aminosulfonyl)-4-methyl-1,3-thiazol-2-yl]-N-methyl-2-[4-(2-yridinyl)phenyl]acetamide mono methanesulfonic acid monohydrate in cell culture medium (71%) and in murine plasma (2.8%). Plasma concentrations remained over the $EC_{90}$ for the entire treatment interval after administration of 40 mg as free base equivalent of crystalline N-[5-(aminosulfonyl)-4-methyl-1,3-thiazol-2-yl]-N-methyl-2-[4-(2-yridinyl)phenyl]acetamide mono methanesulfonic acid monohydrate once daily at steady state. $EC_{90}$ denotes 90% effective concentration.

Figure 11:
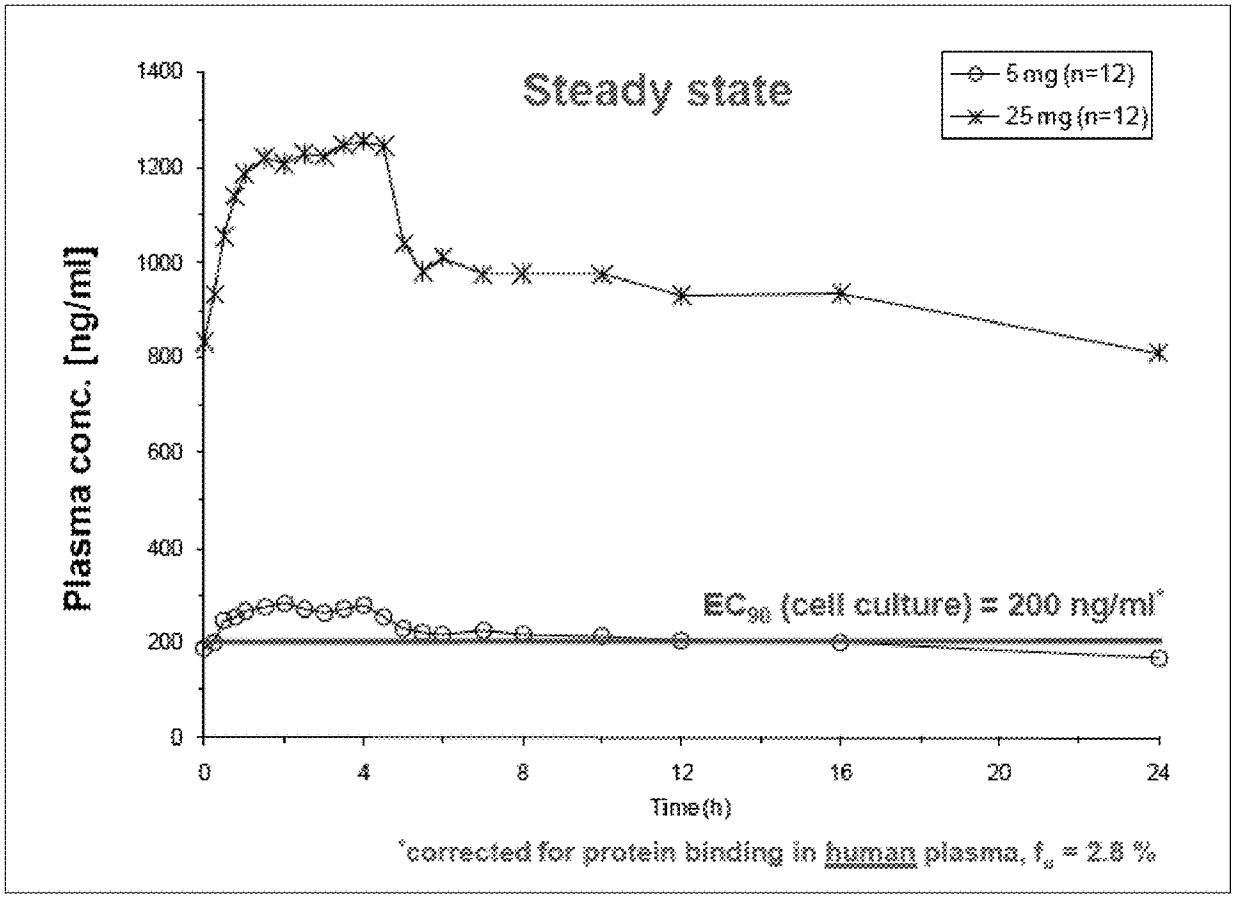

FIG. 11 Shows plasma time curve of the free base of N-[5-(aminosulfonyl)-4-methyl-1,3-thiazol-2-yl]-N-methyl-2-[4-(2-pyridinyl)phenyl]acetamide after administration of tablets containing 5 mg and 25 mg as free base equivalent of crystalline N-[5-(aminosulfonyl)-4-methyl-1,3-thiazol-2-yl]-N-methyl-2-[4-(2-yridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ in fasted, male healthy volunteers (n=12) after multiple dose administration thereof once daily at day 21 (steady state). The two different doses were administered as immediate release tablets and blood was collected at indicated time points after administration. The free base concentration was measured by HPLC in plasma. The $EC_{90}$ derived from cell culture was corrected for protein binding taking into account the fraction unbound of N-[5-(aminosulfonyl)-4-methyl-1,3-thiazol-2-yl]-N-methyl-2-[4-(2-yridinyl)phenyl]acetamide mono methanesulfonic acid monohydrate in cell culture medium (71%) and in murine plasma (2.8%). Plasma concentrations remained over the $EC_{90}$ for the entire treatment interval after administration of 25 mg as free base equivalent of crystalline N-[5-(aminosulfonyl)-4-methyl-1,3-thiazol-2-yl]-N-methyl-2-[4-(2-yridinyl)phenyl]acetamide mono methanesulfonic acid monohydrate once daily at steady state. $EC_{90}$ denotes 90% effective concentration.

Figure 12:
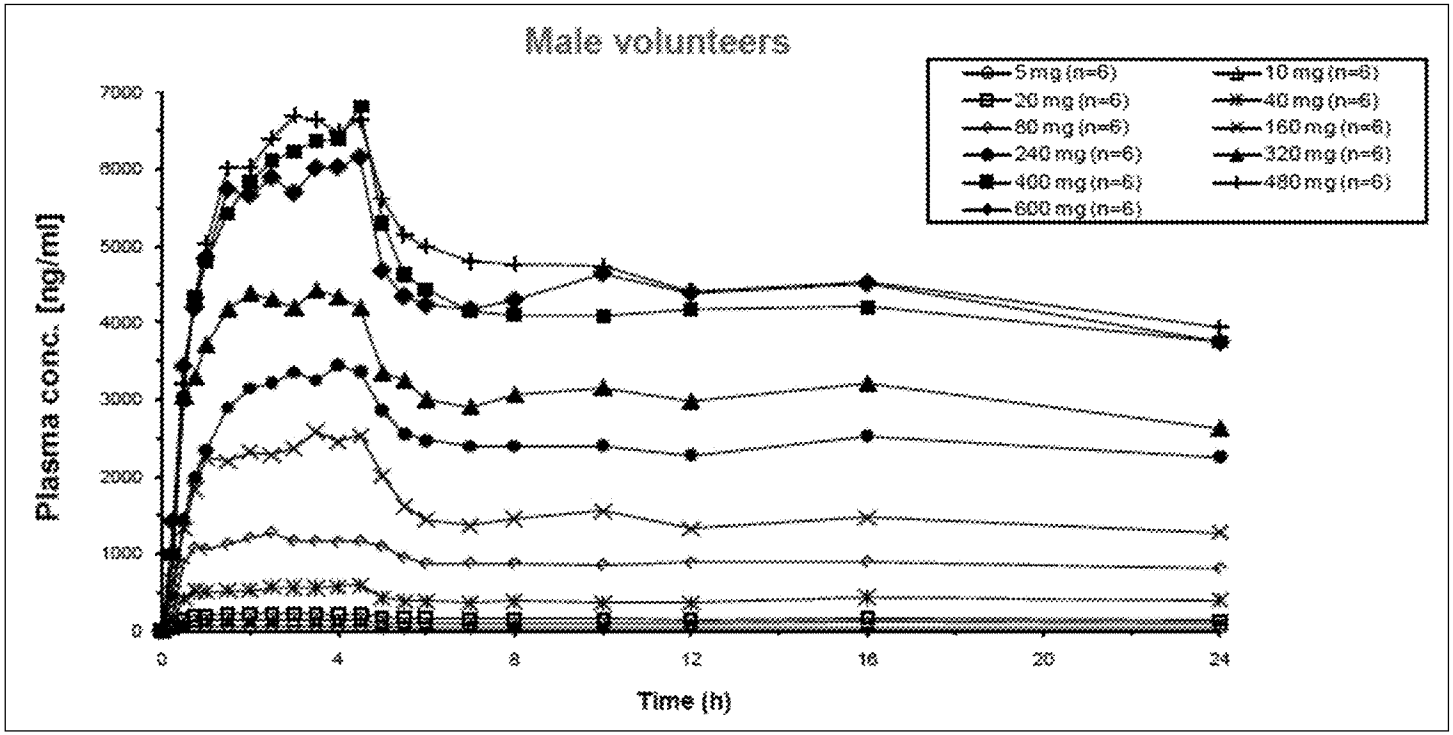

FIG. 12 Shows dose proportionality after single dose administration to fasted male healthy volunteers (n=6) of up to 400/480 mg as free base equivalent of crystalline N-[5-(aminosulfonyl)-4-methyl-1,3-thiazol-2-yl]-N-methyl-2-[4-(2-yridinyl)phenyl]acetamide mono methanesulfonic acid monohydrate, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$. Terminal half-life ($t_{1/2z}$) is between 52 h and 85 h.

Figure 13:
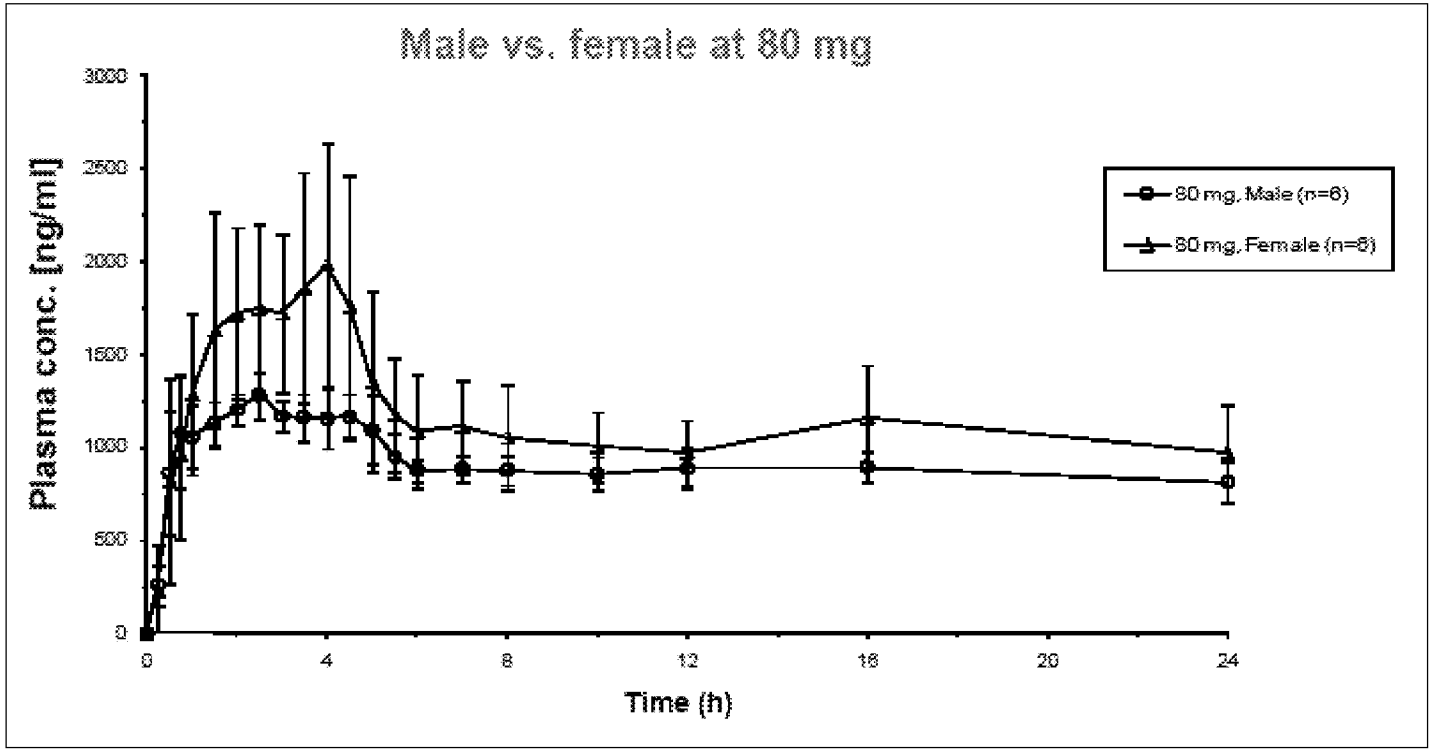

FIG. 13 Shows that the total exposure of the free base of N-[5-(aminosulfonyl)-4-methyl-1,3-thiazol-2-yl]-N-methyl-2-[4-(2-yridinyl)phenyl]acetamide, resultant from crystalline mono methanesulfonic acid monohydrate administration with 80 mg single dose as free base equivalent, wherein the particle size distribution is preferably defined by d(0.1) from 2 to 100 μm, d(0.5) from 30 to 210 μm and d(0.9) from 70 to 400 μm with a specific surface area of the particles less than 1.0 $m^2/g$, and more preferably defined by d(0.1) from 10 to 75 μm, d(0.5) from 100 to 175 μm, d(0.9) from 200 to 350 μm with a specific surface area of the particles less than 0.3 $m^2/g$ to woman is higher (triangle) compared to males (dots) for n=6. After normalization to body weight no relevant gender differences could be revealed.

The invention claimed is:

1. A composition of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles of the following formula

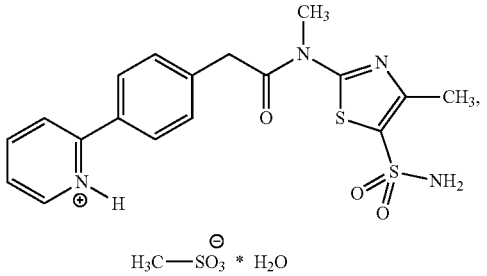

having a purity of >99%, wherein said particles in the composition have a particle size range from 2 μm to 500 μm, a particle size distribution which is defined by d(0.1) from 2 to 100 μm, d(0.5) from 30 to 210 μm and d(0.9) from 70 to 400 μm and a specific surface area of less than 1.0 $m^2/g$.

2. The composition of crystalline N-[5-(aminosulfonyl)-4-methyl-1,3-thiazol-2-yl]-N-methyl-2-[4-(2-pyridinyl)phenyl]acetamide mono methanesulfonic acid monohydrate particles according to claim 1, wherein the N-[5-(aminosulfonyl)-4-methyl-1,3-thiazol-2-yl]-N-methyl-2-[4-(2-pyridinyl)-phenyl]acetamide mono methanesulfonic acid monohydrate particles have a particle size range from larger than 2 μm to 400 μm.

3. The composition of crystalline N-[5-(aminosulfonyl)-4-methyl-1,3-thiazol-2-yl]-N-methyl-2-[4-(2-pyridinyl)phenyl]acetamide mono methanesulfonic acid monohydrate particles according to claim 1, wherein the particles have a particle size distribution which is defined by d(0.1) from 10 to 75 μm, d(0.5) from 100 to 175 μm, d(0.9) from 200 to 350 μm.

4. The composition of crystalline N-[5-(aminosulfonyl)-4-methyl-1,3-thiazol-2-yl]-N-methyl-2-[4-(2-pyridinyl)phenyl]acetamide mono methanesulfonic acid monohydrate particles according to claim 1, wherein the particles have a specific surface area of less than 0.3 $m^2/g$.

5. A combination of the composition of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles according to claim 1 and acetylsalicylic acid, trifluridine, idoxuridine, foscarnet, cidofovir, ganciclovir, aciclovir, penciclovir, valaciclovir, famciclovir and/or valganciclovir.

6. A pharmaceutical composition comprising the composition of crystalline N-[5-(aminosulfonyl)-4-methyl-1,3-thiazol-2-yl]-N-methyl-2-[4-(2-pyridinyl)phenyl]acetamide mono methanesulfonic acid monohydrate particles as defined in claim 1 and at least one pharmaceutically acceptable carrier, excipient, solvent and/or diluent.

7. The pharmaceutical composition according to claim 6, wherein the composition of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles have a particle size range from larger than 2 μm to 400 μm.

8. The pharmaceutical composition according to claim 6, wherein the composition of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles have a particle size distribution which is defined by d(0.1) from 10 to 75 μm, d(0.5) from 100 to 175 μm, d(0.9) from 200 to 350 μm.

9. The pharmaceutical composition according to claim 6, wherein the composition of crystalline N-[5-(aminosulfonyl)-4-methyl-1,3-thiazol-2-yl]-N-methyl-2-[4-(2-pyridinyl)-phenyl]acetamide mono methanesulfonic acid monohydrate particles have a specific surface area of less than 0.3 $m^2/g$.

10. A combination of the pharmaceutical composition according to claim 6 and acetylsalicylic acid, trifluridine, idoxuridine, foscarnet, cidofovir, ganciclovir, aciclovir, penciclovir, valaciclovir, famciclovir and/or valganciclovir.

11. The pharmaceutical composition according to claim 6, which is effective to achieve an absolute bioavailability of 70%±30% of the free base of N-[5-(aminosulfonyl)-4-methyl-1,3-thiazol-2-yl]-N-methyl-2-[4-(2-pyridinyl)-phenyl]acetamide, when administered in said composition containing at least 25 mg as free base equivalent of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate.

12. The pharmaceutical composition according to claim 6, which is effective to achieve a mean maximum blood plasma concentration (mean $C_{max}$) of the free base of N-[5-(aminosulfonyl)-4-methyl-1,3-thiazol-2-yl]-N-methyl-2-[4-(2-pyridinyl)-phenyl]acetamide in a subject of at least one of a) 608±184 ng/ml for a 40 mg dosage as free base equivalent of crystalline N-[5-(aminosulfonyl)-4-methyl-1,3-thiazol-2-yl]-N-methyl-2-[4-(2-pyridinyl)-phenyl]mono methanesulfonic acid monohydrate, said dosage being a single oral dose administered;

b) 1306±125 ng/ml for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

c) 2613±1341 ng/ml for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

d) 3600±752 ng/ml for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

e) 4648±1813 ng/ml for a 320 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

f) 6926±1656 ng/ml for a 400 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a single oral dose administered;

g) 6921±2190 ng/ml for a 480 mg dosage as free base equivalent of crystalline N-[5-(aminosulfonyl)-4-methyl-1,3-thiazol-2-yl]-N-methyl-2-[4-(2-pyridinyl)- phenyl]acetamide mono methanesulfonic acid monohydrate, said dosage being a single oral dose administered.

13. The pharmaceutical composition according to claim 6, which is effective to achieve a mean maximum blood plasma concentration (mean $C_{max}$) of the free base of N-[5-(aminosulfonyl)-4-methyl-1,3-thiazol-2-yl]-N-methyl-2-[4-(2-pyridinyl)-phenyl]acetamide in a subject of at least one of a) 608±184 ng/ml for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 10090±3114 ng-h/ml in a subject for a 40 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 72±3 h on average; said dosage being a single oral dose administered;

b) 1306±125 ng/ml for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 21940±2057 ng-h/ml in a subject for a 80 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 74±5 h on average; said dosage being a single oral dose administered;

c) 2613±1341 ng/ml for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to a achieve an $AUC_{0-24h}$ of 40470±16700 ng-h/ml in a subject for a 160 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 63±6 h on average; said dosage being a single oral dose administered;

d) 3600±752 ng/ml for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 59610±12770 ng-h/ml in a subject for a 240 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 64±5 h on average; said dosage being a single oral dose administered;

e) 4648±1813 ng/ml for a 320 mg dosage as free base equivalent of crystalline N-[5-(aminosulfonyl)-4-methyl-1,3-thiazol-2-yl]-N-methyl-2-[4-(2-pyridinyl) phenyl]acetamide mono methanesulfonic acid monohydrate and/or effective to achieve an $AUC_{0-24h}$ of 76250±27630 ng-h/ml in a subject for a 320 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 57±3 h on average; said dosage being a single oral dose administered;

f) 6926±1656 ng/ml for a 400 mg dosage as free base equivalent of crystalline N-[5-(aminosulfonyl)-4-methyl-1,3-thiazol-2-yl]-N-methyl-2-[4-(2-pyridinyl) phenyl]acetamide mono methanesulfonic acid monohydrate and/or effective to achieve an $AUC_{0-24h}$ of 104800±25740 ng-h/ml in a subject for a 400 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 57±4 h on average; said dosage being a single oral dose administered;

g) 6921±2190 ng/ml for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{0-24h}$ of 112800±34260 ng-h/ml in a subject for a 480 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 53±4 h on average; said dosage being a single oral dose administered.

14. The pharmaceutical composition according to claim 6, which is effective to achieve a mean maximum blood plasma concentration at steady state (mean $C_{max,ss}$) of the free base of N-[5-(aminosulfonyl)-4-methyl-1,3-thiazol-2-yl]-N-methyl-2-[4-(2-pyridinyl)-phenyl]acetamide in a subject of at least one of a) 1358±167 ng/ml for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a steady state dose achieved after once daily single doses administered for 21 days;

b) 6358±1701 ng/ml for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a steady state dose achieved after once daily single doses administered for 21 days;

c) 9987±2608 ng/ml for a 200 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, said dosage being a steady state dose achieved after once daily single doses administered for 21 days.

15. The pharmaceutical composition according to claim 6, which is effective to achieve a mean maximum blood plasma concentration at steady state (mean $C_{max,ss}$) of the free base of N-[5-(aminosulfonyl)-4-methyl-1,3-thiazol-2-yl]-N-methyl-2-[4-(2-pyridinyl)-phenyl]acetamide in a subject of at least one of a) 1358±167 ng/ml for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{\tau,ss}$ of 23430±3020 ng-h/ml in a subject for a 25 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 69±6 h on average, said dosage being a steady state dose achieved after once daily single doses administered for 21 days;

b) 6358±1701 ng/ml for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate and/or effective to achieve an $AUC_{\pi,ss}$ of 108800±28610 ng-h/ml in a subject for a 100 mg dosage as free base equivalent of crystalline N-[5-(aminosulfonyl)-4-methyl-1,3-thiazol-2-yl]-N-methyl-2-[4-(2-pyridinyl)-phenyl]acetamide mono methanesulfonic acid monohydrate, and wherein $t_{1/2z}$ is 60±4 h on average, said dosage being a steady state dose achieved after once daily single doses administered for 21 days.

16. The pharmaceutical composition of claim 11, wherein said absolute bioavailability is achieved in a human.

17. The pharmaceutical composition of claim 12, wherein said mean $C_{max}$ is achieved in a human.

18. The pharmaceutical composition of claim 13, wherein said $AUC_{0-24h}$ and $t_{1/2z}$ are achieved in a human.

19. The pharmaceutical composition of claim 15, wherein said $AUC_{\pi,ss}$ and $t_{1/2z}$ are achieved in a human.

20. The pharmaceutical composition of claim 13, wherein said mean $C_{max}$ is achieved in a human.

21. The pharmaceutical composition of claim 14, wherein said mean $C_{max,ss}$ is achieved in a human.

22. The pharmaceutical composition of claim 15, wherein said mean $C_{max,ss}$ is achieved in a human.

*23. Crystalline N-[5-(aminosulfonyl)-4-methyl-1,3-thiazol-2-yl]-N-methyl-2-[4-(2-pyridinyl)-phenyl]acetamide mono methanesulfonic acid monohydrate of the following formula and having a purity of >99%:*

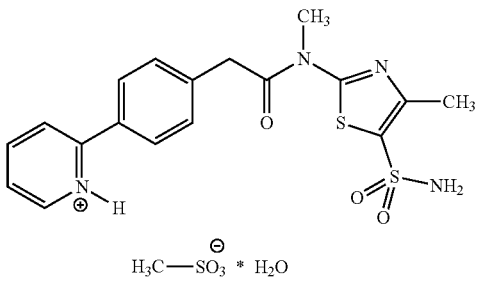

*obtained by a process comprising the following steps*

*a) providing a mixture of an organic solvent and water containing N-[5-(aminosulfonyl)-4-methyl-1,3-thiazol-2-yl]-N-methyl-2-[4-(2-pyridinyl)phenyl]-acetamide,*

*b) adding methanesulfonic acid at an elevated temperature to the mixture of step a to obtain a supersaturated solution of the mesylate of N-[5-(aminosulfonyl)-4-methyl-1,3-thiazol-2-yl]-N-methyl-2-[4-(2-pyridinyl) phenyl]-acetamide,*

*c) optionally adding seed crystals of N-[5-(aminosulfonyl)-4-methyl-1,3-thiazol-2-yl]-N-methyl-2-[4-(2-pyridinyl)phenyl]acetamide mono methane-sulfonic acid monohydrate at an elevated temperature between 30° C. and 90° C. to the supersaturated solution obtained in step b,*

*d) optionally stirring the supersaturated solution obtained in step b or step c,*

*e) cooling the supersaturated solution obtained in step b, step c or step d to room temperature,*

*f) filtering off the resulting crystals and washing the crystals with alcohol/water, and*

*g) optionally drying the crystals under vacuum at a temperature between 20° C. and 60° C.*

*24. The crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to claim 23, wherein the methanesulfonic acid is added in step b over 5 to 15 minutes at the elevated temperature and wherein the resulting mixture is kept at the elevated temperature for 0.5 to 5 hours after completion of the addition of the methanesulfonic acid.*

*25. The crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to claim 23, wherein cooling to room temperature is performed in step e within 1 to 5 hours and the mixture is thereafter stirred at room temperature.*

*26. A method for the treatment of a herpes simplex virus infection, comprising administering to a subject in need thereof an effective amount of the crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to claim 23.*

*27. A pharmaceutical composition containing the crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to claim 23 and one or more pharmaceutically acceptable carriers.*

*28. A pharmaceutical composition containing the crystalline N-[5-(aminosulfonyl)-4-methyl-1,3-thiazol-2-yl]-N-methyl-2-[4-(2-pyridinyl)phenyl]acetamide mono methanesulfonic acid monohydrate according to claim 23 in combination with acetylsalicylic acid, trifluridine, idoxuridine, foscarnet, cidofovir, ganciclovir, aciclovir, penciclovir, valaciclovir, famciclovir and/or valganciclovir, and optionally with one or more pharmaceutically acceptable carriers.*

*29. A method for the treatment of a herpes simplex virus infection, comprising administering to a subject in need thereof an effective amount of the pharmaceutical composition according to claim 27.*

*30. The method according to claim 29, wherein the pharmaceutical composition is administered thrice daily, twice daily, once daily, thrice weekly, twice weekly, or once weekly.*

*31. The crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to claim 23, wherein the organic solvent in step a is selected from the group consisting of MeOH, EtOH, n-PrOH, i-PrOH, acetonitrile, THF and acetone.*

*32. The crystalline N-[5-(aminosulfonyl)-4-methyl-1,3-thiazol-2-yl]-N-methyl-2-[4-(2-pyridinyl)-phenyl]acetamide mono methanesulfonic acid monohydrate according to claim 23, wherein the elevated temperature in step b is between 30° C. and 90° C.*

* * * * *